US008372848B2

(12) United States Patent
Houghten et al.

(10) Patent No.: US 8,372,848 B2
(45) Date of Patent: Feb. 12, 2013

(54) MELANIN-CONCENTRATING HORMONE RECEPTOR ANTAGONISTS AND METHODS OF USE

(75) Inventors: Richard A. Houghten, Solana Beach, CA (US); Colette Dooley, San Diego, CA (US); Adel Nefzi, San Diego, CA (US); Zhiwei Wang, Irvine, CA (US); Oliver Civelli, Irvine, CA (US); Hiroshi Nagasaki, Nagoya (JP)

(73) Assignees: Mixture Sciences, Inc., San Diego, CA (US); The Regents of the University of California, Oakland, CA (US)

( * ) Notice: Subject to any disclaimer, the term of this patent is extended or adjusted under 35 U.S.C. 154(b) by 1180 days.

(21) Appl. No.: 10/593,941

(22) PCT Filed: Mar. 23, 2005

(86) PCT No.: PCT/US2005/009527
§ 371 (c)(1),
(2), (4) Date: Jul. 1, 2008

(87) PCT Pub. No.: WO2005/094817
PCT Pub. Date: Oct. 13, 2005

(65) Prior Publication Data
US 2008/0255218 A1 Oct. 16, 2008

Related U.S. Application Data

(60) Provisional application No. 60/555,820, filed on Mar. 23, 2004.

(51) Int. Cl.
*A61K 31/495* (2006.01)
*A61K 31/4166* (2006.01)
*A61K 31/4168* (2006.01)
*C07D 233/12* (2006.01)
*C07D 239/10* (2006.01)
*C07D 239/12* (2006.01)

(52) U.S. Cl. .............. 514/256; 548/324.5; 544/297; 544/298; 514/392

(58) Field of Classification Search ........... 548/324.5; 514/392, 256; 544/297, 298
See application file for complete search history.

(56) References Cited

U.S. PATENT DOCUMENTS 3,196,152 A * 7/1965 Wright et al. .............. 544/139
5,786,448 A 7/1998 Nefzi et al.

FOREIGN PATENT DOCUMENTS
FR 1516714 3/1968

OTHER PUBLICATIONS

STN Registry search result for Reg. No. 1242982-50-8.*
STN Registry search result for Reg. No. 1229688-46-3.*
STN Registry listing for Reg. No. 1242982-50-8, published Sep. 2010.*
STN Registry listing for Reg. No. 1229688-46-3, published Jul. 2010.*
International Search Report and Written Opinion dated Sep. 19, 2005 in related PCT Application No. PCT/US05/09527.
Kawauchi, et al., Nature 305 5932:321-3 (1983).
Mouri, Peptides 14 3:643-6 (1993).
Vaughan, et al., Endocrinology 125 3:1660-5 (1989).
Bittencourt, et al, J Comp Neurol 319 2:218-45 (1992).
Saito, et al., Nature 400 6741:265-9 (1999).
Mori, et al., Biochem Biophys Res Commun 283 5:1013-8 (2001).
Saito, et al., J Comp Neuro 435 1:26-40 (2001).
Tan, et al., Genomics 79 6:785-92 (2002).
Qu, et al., Nature 380 6571:243-7 (1996).
Kokkotou, et al., Endocrinology 142 2:680-6 (2001).
Stricker_Krongrad, Brain Res Mol Brain Res 92 1-2:43-8 (2001).
Bradley, et al. Am J Physiol Endocrinol Metab 283 3:E584-92 (2002).
Tadayyon, Biochem Biophys Res Commun 275 (2):709-12 (2000).
Kennedy, et al., J Neuroendocrinol 15 3:268-72 (2003).
Murray, et al., J Neuroendocrinol 12 3:217-23 (2000).
Shimada, et al., Nature 396 (6712):670-4 (1998).
Ludwig, et al., J Clin Invest 107 (3):379-86 (2001).
Chen, et al., Endocrinology 143 7:2469-77 (2002).
Nefzi et al. Tetrahedron Letters, 38:931-934 (1997).
Wang et al. J. Biol. Chem., 276:34664-34670, (2001).
Sambrook et al., Molecular Cloning: A Laboratory Manual, Cold Spring Harbor Laboratory, New York (1992).
Ansubel et al., Current Protocols in Molecular Biology, John Wiley and Sons, Baltimore, MD (1998).
Calle et al., N. Engl. J. Med 341:1097-1105 (1999).
Bray et al., Nature 404: 672-677 (2000).
Houghten, 1985, Nefzi et al. Tetrahedron Letters 38:931-934 (1997).
Dorner et al. Bioorg. & Med. Chem., 4:709 (1996).
Ostresh et al. Proc, Nat. Acad. Sci., 91:11138 (1994).
Cuervo et al. In Peptides, 1994, Proceedings of the 23rd European Peptide Symposium (Maia,H.L.S, ed): 465-466 (1995).
Majer and Randad, J, Org. Chem., 59:1937-1938 (1994).
Kim et al., Tetrahedron Lett., 37:5309 (1996).
Houghten et al. Int. J. Pep. Prot. Res., 27:673 (1986).
Krchnak et al. Coll. Czech. Chem. Commun., 53:2542 (1988).

* cited by examiner

*Primary Examiner* — Kamal Saeed
*Assistant Examiner* — Janet L Coppins
(74) *Attorney, Agent, or Firm* — Robert D. Buyan; Stout, Uxa, Buyan & Mullins, LLP

(57) ABSTRACT

This invention relates generally to N-benzylamino cyclic thioureas, pharmaceutical compositions containing them, and their use as antagonists of melanin-concentrating hormone receptor (MCH receptor).

10 Claims, 12 Drawing Sheets

MELANIN-CONCENTRATING HORMONE RECEPTOR ANTAGONISTS AND METHODS OF USE

RELATED APPLICATION

This application claims priority to U.S. Provisional Patent Application No. 60/555,820 entitled "Melanin-Concentrating Hormone Receptor Antagonists and Methods of Use" filed on Mar. 23, 2004, the entirety of which is expressly incorporated herein by reference.

STATEMENT REGARDING GOVERNMENT FUNDING

This invention was made with government support under Grant No. MH-60231, awarded by the National Institute of Mental Health. The Government has certain rights in this invention.

BACKGROUND OF THE INVENTION

Obesity is a major health concern in most industrialized nations. Obesity correlates with, and can trigger, the onset of serious medical conditions, including hypertension, diabetes, cardiovascular disease and psychological maladjustments. With obesity affecting more than one third of Americans and more than one half of certain populations (for example, Hispanic females), its important role in overall morbidity and mortality is clear. Although identification of individuals afflicted with this problem is straightforward, treatment methods have proven elusive. Initial failure rates for treatment of obesity are high, and relapse after successful weight loss is common.

Combinations of diet, exercise, surgery and various drug therapies are currently being used to decrease body fat in obese individuals. Drug therapy for weight loss generally falls into the categories of appetite suppressants and agents that decrease food absorption. Unfortunately, such drugs have disadvantages including abuse potential (for example, benzphetamine and phendimetrazine); serious permanent side effects (for example, fenfluramine, which was withdrawn from the market because it caused valvular heart disease); failure in long-term efficacy (for example, fluoxetine and other selective serotonin reuptake inhibitors) and other side effects, such as the flatulence, increased stool frequency and increased urgency associated with drugs that decrease food absorption. Accordingly, there exists a need for identifying compounds for treating obesity and related disorders. The present invention satisfies this need and provides related advantages as well.

SUMMARY OF THE INVENTION

This invention relates generally to N-benzylamino cyclic thioureas according to Formula I, pharmaceutical compositions containing them, and their use as antagonists of melanin-concentrating hormone receptor (MCH receptor).

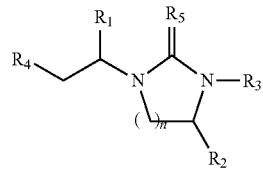

Formula I wherein $R_1$ and $R_2$ are selected from H and a straight or branched, saturated or unsaturated, cyclic or acyclic, chiral or achiral hydrocarbyl group with up to 20 carbon atoms, optionally substituted with hydroxy, alkoxy, amino, substituted amino, thio, alkylthio, guanidino, ureido, heterocyclyl, such as 2-pyrrolidinyl and 2-(4-hydroxypyrrolidinyl) and heteroaryl, such as 3-indolyl and 4(5)-imidazolyl;

$R_3$ is a straight or branched, saturated or unsaturated, cyclic or acyclic, chiral or achiral hydrocarbyl group with up to 20 carbon atoms, optionally substituted with halo, haloalkyl, hydroxy, alkyl, alkoxy, alkylenedioxy, amino, substituted amino, aminoalkyl, thio, alkylthio, guanidino, ureido, heterocyclyl, heteroaryl, and heteroarylthio and one or more methylene groups in the hydrocarbyl group can be replaced by an oxygen atom;

$R_4$ is a substituted amino, $-NR_6R_7$, wherein $R_6$ and $R_7$ are selected from H and straight or branched, saturated or unsaturated, cyclic or acyclic, chiral or achiral hydrocarbyl group with up to 20 carbon atoms; $R_6$ and $R_7$, with inclusion of N, may combine to form a heterocyclic ring such as indolinyl; having the formula

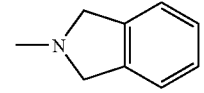

$R_5$ is selected from O, S, NH, N-alkyl, N-alkenyl, N-alkynyl, N-cycloalkyl, N-aryl and N-aralkyl; and n is 1-3.

BRIEF DESCRIPTION OF THE DRAWINGS

FIG. 3A shows change in fluorescence in MCH1R expressing HEK-293T cells pre-treated with various concentration of TPI 1361-17 ten minutes prior being stimulated by 1 nM MCH. FIG. 3B shows dose response curves obtained for inhibition of MCH-induced fluorescence in MCH1R expressing HEK-293T cells by increasing concentrations of TPI 1361-17. FIG. 3C shows a Schild plot of TPI 1361-17 antagonism. Data are mean ±S.E.M., n=3. FIG. 3D shows effects of TPI 1361-17 on [$^{125}$I] MCH binding to membrane fractions of MCH1R expressing HEK-293T. The data representative of three separate experiments with similar results are shown.

FIG. 6A shows results when TPI 1361-17 was administered at the beginning of phase cycle after one hour of food-deprivation, FIG. 6B shows results when TPI 1361-17 was administered at the beginning of dark phase after four hours of food deprivation. FIG. 6C shows results when TPI 1361-17 was administered at the beginning of light phase after overnight food deprivation. Each column expresses the mean value of food intake during each period of time as illustrated with S.E.M. *$p<0.05$; ANOVA/Bonferoni multiple comparison test for the effect of TPI 1361-17 versus ACSF.

DETAILED DESCRIPTION OF THE INVENTION

This invention relates generally to N-benzylamino cyclic thioureas, pharmaceutical compositions containing them, and their use as antagonists of melanin-concentrating hormone receptor (MCH receptor).

Melanin-concentrating hormone (MCH) is a cyclic, 19-amino-acid peptide isolated from salmon pituitary as a melanophore concentrating factor (Kawauchi, et al., Nature 305 5932:321-3 (1983), that is also present in rat and human (Mouri, Peptides 14 3:643-6 (1993); Vaughan, et al., Endocrinology 125 3:1660-5 (1989). In the mammalian brain, MCH is predominantly expressed in the perikarya of the lateral hypothalamic area (LHA), and the zona incerta (ZI) and projects widely throughout the CNS (Bittencourt, et al, J Comp Neurol 319 2:218-45 (1992); Vaughan, et al., Endocrinology 125 3:1660-5 (1989)). MCH is known to interact with two receptors, MCH1R (Saito, et al., Nature 400 6741:265-9 (1999)) and MCH2R (Mori, et al., Biochem Biophys Res Commun 283 5:1013-8 (2001)). MCH1R is expressed in the brain regions in which MCH fibers were identified, in particular in centers that modulate feeding behavior and olfactory learning (Saito, et al., J Comp Neuro 435 1:26-40 (2001); Saito, et al., Nature 400 6741:265-9 (1999)), and in some peripheral tissues (Mori, et al., Biochem Biophys Res Commun 283 5:1013-8 (2001)). MCH2R, identified on the basis of its sequence similarity to MCH1R, is absent in rodents (Tan, et al., Genomics 79 6:785-92 (2002)).

In mammals, MCH has been shown to regulate food consumption and energy metabolism. Central administration of MCH has been shown to promote feeding (Qu, et al., Nature 380 6571:243-7 (1996)), while MCH1R mRNA levels rise as a result of starvation and leptin deficiency (Kokkotou, et al., Endocrinology 142 2:680-6 (2001)) and MCH circulatory levels are high in obese Zucker rats (Stricker_Krongrad, Brain Res Mol Brain Res 92 1-2:43-8 (2001)). MCH also stimulates insulin and leptin release in insulinoma cell lines and 3T3-L1 adipose cells, respectively (Bradley, et al. Am J Physiol Endocrinol Metab 283 3:E584-92 (2002); Tadayyon, Biochem Biophys Res Commun 275 (2):709-12 (2000)) and regulates pituitary hormones (Kennedy, et al., J Neuroendocrinol 15 3:268-72 (2003); Murray, et al., J Neuroendocrinol 12 3:217-23 (2000)). Mice devoid of MCH are lean and hypophagic (Shimada, et al., Nature 396 (6712):670-4 (1998), while mice over-expressing MCH are obese and hyperphagic (Ludwig, et al., J Clin Invest 107 (3):379-86 (2001)). Genetic disruption of MCH1R on the other hand results in mice that are surprisingly hyperphagic, but also hypermetabolic, and obesity-resistant (Chen, et al., Endocrinology 143 7:2469-77 (2002)). Thus, the MCH receptor has an important role in regulating food intake, adipocyte function and energy metabolism.

Figure 1:
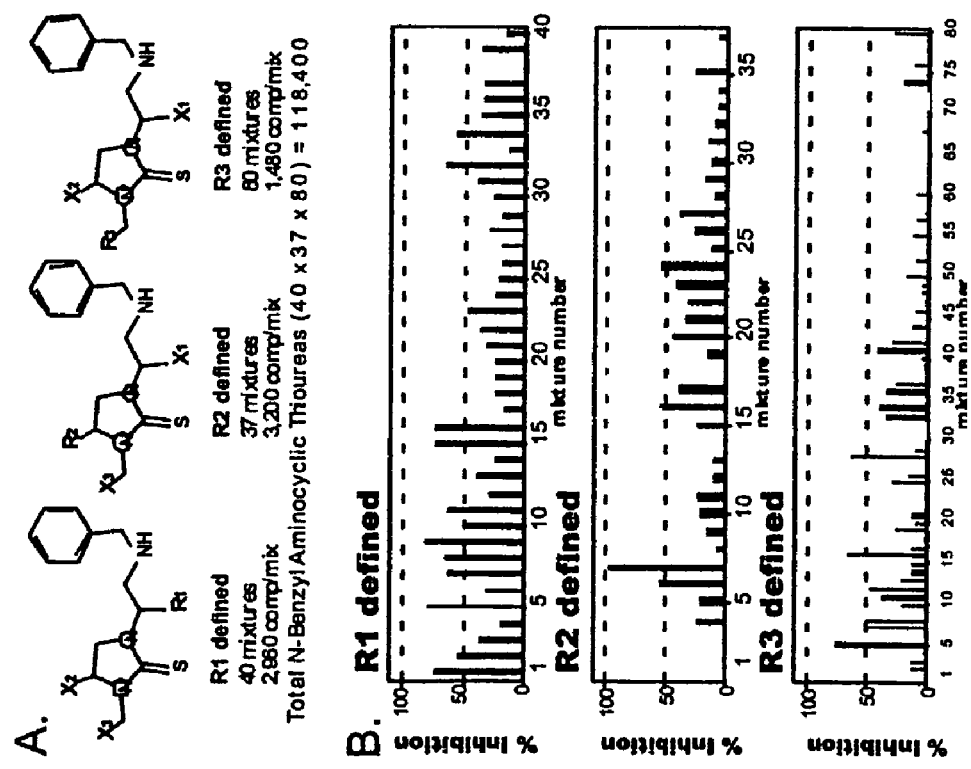
FIG. 1A shows a representation of the N-benzylamino cyclic thiourea positional scanning combinatorial library (PS-SCL). R is defined as a single block; X is a mixture of building blocks.
FIG. 1B shows a profile of the inhibitory activity of the PS-SCL on 30 nM MCH-induced $Ca^{2+}$ mobilization on MCH1R expressing CHO cells. Each graph represents the screening data for all the mixtures with the same one-position defined. By way of example, graph "$R_1$ defined" represents the data for all 40 mixture samples that have $R_1$, defined with a single building block. The bars show the % inhibition by a single mixture at 0.5 μg/ml. A representative data set from three individual assays is shown.

The present invention relates to the discovery of MCH receptor antagonists. The MCH receptor antagonists of the invention were identified by screening of an N-benzylamino cyclic thiourea library for compounds that inhibited MCH-induced $Ca^{2+}$ mobilization in CHO or HEK 293T cells expressing the rat MCH1R. As is shown in FIG. 1, several compounds that inhibited MCH-induced $Ca^{2+}$ mobilization were identified. One of these compounds, which is identified as TPI 1361-17 (Formula IV), exhibited an $IC_{50}$ value of 6.1 nM at 1 nM MCH and completely displaced $[^{125}I]$ MCH binding to rat MCH1R. This compound displayed no affinity to human MCH2R and other peptide GPCRs.

To demonstrate efficacy in vivo, TPI 1361-17 was tested for its ability to block MCH-induced food intake. MCH and TPI 1361-17 were injected into the lateral ventricle of SD rats at the beginning of the light phase, when MCH shows maximal effect, as is described in Example IV. TPI 1361-17 was demonstrated to reduce MCH-induced food intake up to 75% in dose dependent manner. This effect lasted for over 4h, suggesting that this compound remains active in the CNS for at least that period of time. This treatment did not affect locomotion or fine movements, and did not result in ataxic movements.

As is also described in Example IV, the effects of TPI 1361-17 on spontaneous food intake were tested after central administration. It was found that TPI 1361-17 treatment reduced food intake significantly (37%) over the first 30 minutes after administration and in rats that had been starved for a short period of time (1 h). Therefore, the inventors have discovered that the MCH receptor antagonists of formula I are efficacious in reducing food intake in animals, and thus, can be useful for the treatment of a condition associated with MCH receptor, such as obesity, diabetes, eating disorders and related conditions.

The present invention is directed generally to compounds useful as MCH receptor antagonists having the following structure (Formula I), or a pharmaceutically acceptable salt thereof, or ester, amide, carbamate or a related prodrug derivative thereof. The compounds of this invention can have several asymmetric carbon atoms simultaneously and therefore can exist as stereoisomers having different configurations (R or S form). These stereoisomers and their racemic mixtures are also included within the compounds of this invention. If appropriate, the compounds according to the invention, in addition to chiral stereoisomers, can be present as mixtures of different possible geometric stereoisomeric forms, such as, for example, E and Z and any desired mixtures of these isomers. Therefore, all stereoisomers of structure of Formula (I) are included within the scope of this invention:

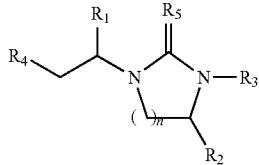

Formula I wherein $R_1$ and $R_2$ are selected from H and a straight or branched, saturated or unsaturated, cyclic or acyclic, chiral or achiral hydrocarbyl group with up to 20 carbon atoms, optionally substituted with hydroxy, alkoxy, amino, substituted amino, thio, alkylthio, guanidino, ureido, heterocyclyl, such as 2-pyrrolidinyl and 2-(4-hydroxypyrrolidinyl) and heteroaryl, such as 3-indolyl and 4(5)-imidazolyl;

$R_3$ is a straight or branched, saturated or unsaturated, cyclic or acyclic, chiral or achiral hydrocarbyl group with up to 20 carbon atoms, optionally substituted with halo, haloalkyl, hydroxy, alkyl, alkoxy, alkylenedioxy, amino, substituted amino, aminoalkyl, thio, alkylthio, guanidino, ureido, heterocyclyl, heteroaryl, and heteroarylthio and one or more methylene groups in the hydrocarbyl group can be replaced by an oxygen atom;

$R_4$ is a substituted amino, —$NR_6R_7$, wherein $R_6$ and $R_7$ are selected from H and straight or branched, saturated or unsaturated, cyclic or acyclic, chiral or achiral hydrocarbyl group with up to 20 carbon atoms; $R_6$ and $R_7$, with inclusion of N, may combine to form a heterocyclic ring such as indolinyl, having the formula

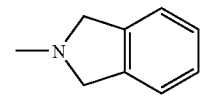

$R_5$ is selected from O, S, NH, N-alkyl, N-alkenyl, N-alkynyl, N-cycloalkyl, N-aryl and N-aralkyl; and n is 1-3.

In embodiments of this invention, representative $R_1$ and $R_2$ groups, which can be present as R or S and E or Z stereoisomer include, alkyl such as methyl, ethyl, 1-propyl, 2-propyl, 2-methylpropyl, 2-butyl; cycloalkyl alkyl such as cyclopentylmethyl and cyclohexylmethyl; aryl such as phenyl, aralkyl such as benzyl, 4-hydroxybenzyl, 1- and 2-naphthylmethyl, aminoalkyl such as aminoethyl, aminopropyl, aminobutyl, benzylaminoethyl, benzylaminopropyl, guanidinopropyl and ureidopropyl, hydroxyalkyl such as hydroxymethyl and 1-hydroxyethyl, thioalkyl such as thiomethyl, alkylthioalkyl such as methylthiomethyl and heteroaryl alkyl such as 3-indolylmethyl and 4(5)-imidazolylmethyl, or a prodrug of the amino and hydroxy functionalities.

Representative $R_3$ groups include, for example, alkyl, such as ethyl, 1-propyl, 2-propyl, 2-methylpropyl, 2,2-dimethylpropyl, butyl, 2-methylbutyl, 3-methylbutyl, 3,3-dimethylbutyl, pentyl, 3-methylpentyl, 4-methylpentyl, heptyl, cycloalkyl alkyl, for example, 2-methylcyclopropylmethyl, cyclobutylmethyl, cyclopentylmethyl, cyclohexylmethyl, 4-methylcyclohexylmethyl, 4-(2-methylpropyl)cyclohexylmethyl, cycloheptylmethyl, abietylmethyl, cyclopentylethyl, cyclohexylethyl, 4-methylcyclohexylethyl, dicyclohexylethyl, adamantylethyl, cyclopentylpropyl, cyclohexylpropyl, cyclohexylbutyl, aralkyl and substituted aralkyl, for example, benzyl, 2-aminobenzyl, 4-aminobenzyl, 2-chloro-4-aminobenzyl, 2-chloro-5-aminobenzyl, 3-dimethylaminobenzyl, 4-dimethylaminobenzyl, 3-methylbenzyl, 4-methylbenzyl, 3,5-bis-trifluoromethylbenzyl, 1-phenyl-1-cyclopropylmethyl, phenethyl, 4-aminophenethyl, 3-bromophenethyl, 3-fluorophenethyl, 3-methoxyphenethyl, 3-methylphenethyl, 3-trifluoromethylphenethyl, 4-bromophenethyl, 4-ethoxyphenethyl, 4-methoxyphenethyl, 4-methylphenethyl, 4-(2-methylpropyl)phenyl-1-methylethyl, 2,4-diaminophenethyl, 3,4-dichlorophenethyl, 3,4-dimethoxyphenethyl, 3,4-methylenedioxy phenethyl, 3,5-bis-trifluoromethylphenethyl, 4-biphenylylethyl, phenylpropyl, 4-chlorophenylpropyl, 4-aminophenylpropyl, 3,4-dimethoxyphenylpropyl, 3,3-diphenylpropyl, 2-methyl-1-phenylpropyl, 2-trifluoromethylphenylpropyl, 2-phenylbutyl, 3-phenylbutyl, 4-phenylbutyl and heteroaryl alkyl, for example, 3-indolylethyl, 2-methyl-4-amino-1-imidazolylpropyl and 2-pyridylthioethyl.

In an embodiment, $R_4$ is a substituted amino, —$NR_6R_7$, wherein $R_6$ and $R_7$, for example, is an alkyl, substituted alkyl, cycloalkyl, substituted cycloalkyl, aralkyl or substituted aralkyl or $R_6$ and $R_7$, with inclusion of N, may combine to form a heterocyclic ring such as indolinyl, having the formula

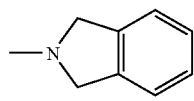

and $R_1$, $R_2$, $R_3$, $R_5$ and n are as defined earlier

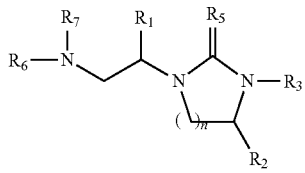

Formula II

Formula II

An exemplary compound having a substituted amino in which $R_6$ is a phenylmethyl (benzyl), $R_7$ is a H, $R_5$ is S and $R_1$, $R_2$, $R_3$, and n are as defined earlier:

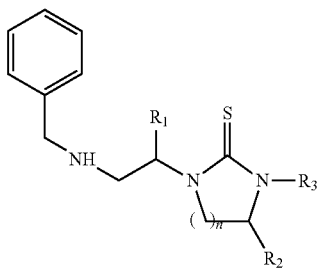

Formula III

An exemplary compound in which $R_1$ is (S)-methyl; $R_2$ is (S)-guanidinopropyl; $R_3$ is 3-fluorophenethyl; $R_4$ is phenylmethylamino; $R_5$ is S and n is 1 is:

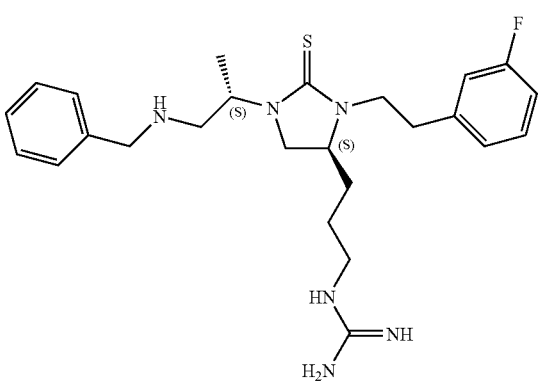

Formula IV (TPI1361-17)

An exemplary compound in which $R_2$ is an alkylaminoalkyl group, n is 1 and $R_1$, $R_3$, $R_4$ and $R_5$ are as defined earlier is:

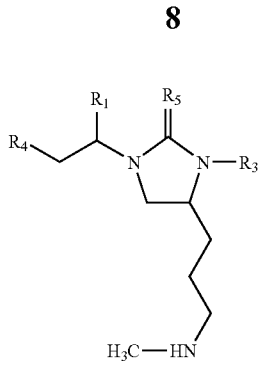

Formula V

Figure 2:
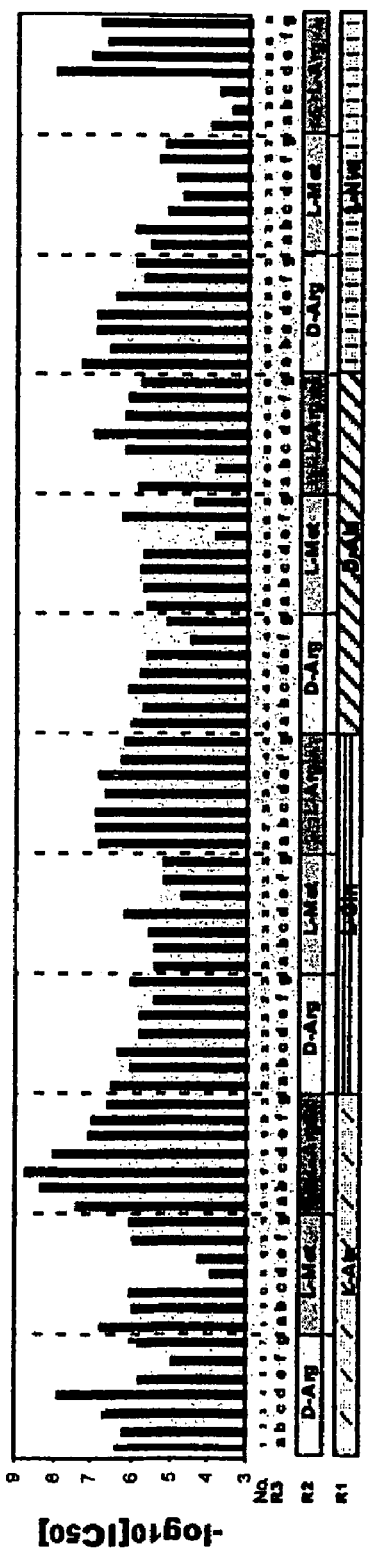
FIG. 2 shows the inhibitory activity of a series of 84 compounds individually synthesized based on the profile of the library screening. $IC_{50}$ values of each compound inhibiting 30 nM MCH-induced $Ca^{2+}$ mobilization in MCH1R expressing CHO cells are indicated. Functionalities at the three diversity positions ($R_1$-$R_3$) for each compound are illustrated. For $R_3$ position, each letter represents organic acids as follows: a; 3-Bromophenylacetic Acid, b; Phenylacetic Acid, c; 3-Fluorophenylacetic Acid, d; 4-Fluorophenylacetic Acid, e; 3,5-Bis (trifluoromethyl)phenylacetic acid, f; 3-Methylphenylacetic Acid, and g; 4-Methylphenylacetic acid.

The MCH receptor antagonist activities of exemplary compounds of the invention wherein $R_1$ is selected from a (S)-methyl, (S)-benzylaminopropyl, (R)-Methyl, and (S)-propyl; $R_2$ is selected from (R)-guanidinopropyl, (S)-guanidinopropyl or (S)-methylthiomethyl; $R_3$ is selected from 3-bromophenethyl, phenethyl, 3-fluorophenethyl, 4-fluorophenethyl, 3,5 bis-(trifluoromethyl)phenethyl, and 4-methylphenethyl; $R_4$ is phenylmethylamino; and $R_5$ is S, are shown in FIG. 2.

As used herein, the term "hydrocarbyl" means a group derived by abstracting a hydrogen atom from a hydrocarbon having only carbon and hydrogen atoms. For example, a hydrocarbyl group can have from 1 to 20 carbon atoms, which can represent a straight or branched, cyclic or acyclic and saturated or unsaturated structural arrangement of the carbon and hydrogen atoms. Such a structure can include one or more asymmetric centers and exhibit chirality. Furthermore, the term "hydrocarbyl" includes alkyl, alkenyl, alkynyl, cycloalkyl, cycloalkenyl, aryl, aralkyl and the like.

As used herein, the term "substituted hydrocarbyl" means a hydrocarbyl group wherein one or more of the hydrogen and/or the carbon atoms are replaced by a functional group such as halo, haloalkyl, amino, alkyl, alkoxy, aryl, aralkyl, hydroxy, hydroxyalkyl, aminoalkyl, alkylamino, thio, alkylthio and the like or by a heteroatom such as nitrogen, oxygen or sulfur atom.

The term "heteroatom" as used herein means an atom of any element other than carbon or hydrogen. heteroatoms are nitrogen, oxygen and sulfur.

As used herein, the term "alkyl" means saturated aliphatic hydrocarbyl group, including straight-chain alkyl groups, branched-chain alkyl groups, cycloalkyl (alicyclic or "saturated cyclic hydrocarbyl") groups, alkyl substituted cycloalkyl groups, and cycloalkyl substituted alkyl groups. The saturated cyclic hydrocarbons, from which the cycloalkyl group is derived, can be single- or multi-ring structures. The term "unsaturated cyclic hydrocarbon" is used to describe a non-aromatic carbocycle with at least one double bond, which affords cycloalkenyl groups such as, for example, cyclopentenyl, cyclohexenyl, etc. and substituted analogues thereof. These cyclic hydrocarbons can be single- or multi-ring structures. In embodiments, a straight chain or branched chain alkyl has 20 or fewer carbon atoms in its backbone (e.g., $C_1$-$C_{20}$ for straight chain, $C_3$-$C_{20}$ for branched chain), and more preferably 12 or fewer. Likewise, cycloalkyls have from 3-10 carbon atoms in their ring structure, and more preferably have 5, 6 or 7 carbons in the ring structure. Exemplary alkyl groups include methyl, ethyl, 1-propyl, 2-propyl, 2-methylpropyl, 2-butyl, 2,2-dimethylethyl, pentyl, hexyl, cyclopentyl, cyclohexyl, 4-methylcyclohexyl, "bridged" rings joined through non-adjacent atoms such as adamantyl, norbornyl, and the like. An alkyl group can be optionally substituted with one or more substituents selected from the group consisting of hydroxy, alkoxy, halo, haloalkyl, amino, mono- and dialkyl amino, thio and alkylthio.

As used herein, the term "alkenyl" means a straight chain, branched or cyclic unsaturated hydrocarbyl group containing at least one carbon carbon double bond. For example, an alkenyl group can have 2 to 20 carbons, preferably 2 to 10 carbons and most preferably 2 to 6 carbons. An alkenyl group can optionally be substituted with one or more substituents as exemplified under "alkyl".

As used herein, the term "alkynyl" means a straight chain or branched unsaturated hydrocarbyl group containing at least one carbon carbon triple bond. For example, an alkynyl group can have 2 to 20 carbons, preferably 2 to 10 carbons and most preferably 2 to 5 carbons. An alkynyl group can optionally be substituted with one or more substituents as exemplified under "alkyl".

As used herein, the term "aryl" includes 5-, 6- and 7-membered single-ring aromatic groups that can include from zero ("aryl carbocycles" or "carbocyclic aryls") to four heteroatoms ("heteroaryl") or a combination of the two (referred to as "aryl heterocycles" or "heterocyclic aryls" or "heteroaromatics"), for example, phenyl, pyrrolyl, furyl, thienyl, imidazolyl, oxazolyl, thiazolyl, triazolyl, pyrazolyl, pyridinyl, pyrazinyl, pyridazinyl, pyrimidinyl, tetrazolyl and the like. The aromatic ring can be substituted at one or more ring positions with such substituents as described above, for example, halo, haloalkyl such as $CF_3$, alkyl, aryl, aralkyl, alkenyl, alkynyl, cycloalkyl, hydroxy, alkoxy, amino, thio, alkylthio, guanidine, ureido, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, aryls and/or heterocyclyls, such as naphthyl, tetralinyl, indolyl or the like. The linear aryl substituted aryl, such as biphenyls and terphenyls, can be linked at 1,2-, 1,3- or 1,4-positions. The terms ortho, meta and para apply to 1,2-, 1,3- and 1,4-disubstituted benzenes, respectively. For example, the names 1,2-difluorobenzene and ortho-difluorobenzene are synonymous.

As used herein, the term "heterocyclyl" refers to 3- to 10-membered saturated or unsaturated ring structures, more preferably 3- to 7-membered rings, whose ring structures include one to four heteroatoms. Heterocycles can also be polycycles ("heteroaromatics" or "heteroaryls"). Heterocyclyl groups include, for example, thienyl, thianthrenyl, furyl, pyryl, isobenzofuryl, chromenyl, xanthenyl, pyrrolyl, imidazolyl, pyrazolyl, isothiazolyl, isoxazolyl, pyridinyl, pyrazinyl, pyrimidinyl, pyridazinyl, indolizinyl, isoindolyl, indolyl, indazolyl, purinyl, quinolizinyl, isoquinolinyl, quinolinyl, phthalazinyl, naphthyridinyl, quinoxalinyl, quinazolinyl, cinnolinyl, pteridinyl, carbazolyl, carbolinyl, phenanthridinyl, acridinyl, phenanthrolinyl, phenazinyl, phenothiazinyl, phenoxazinyl, pyrrolidinyl, oxolanyl, thiolanyl, oxazolyl, piperidinyl, piperazinyl, morpholinyl, tetrahydrofuryl, and the like. The heterocyclic ring can be substituted at one or more positions with such substituents as described above, as for example, halo, haloalkyl, alkyl, aralkyl, alkenyl, alkynyl, cycloalkyl, hydroxy, amino, thio, alkylthio, a heterocyclyl, an aromatic or heteroaromatic moiety, or the like.

As used herein, the term "heteroaryl" primarily refers to aromatic rings in which one or more carbon atoms of the aromatic ring(s) are replaced by a heteroatom such as nitrogen, oxygen or sulfur. Heteroaryl refers to structures, which can be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. As used herein, groups such as thienyl, pyridinyl, isoxazolyl, pyrazolyl, furyl, etc. or benzo-fused analogues of these rings, such as indolyl, are defined by the term "heteroaryl."

As used herein, the term "heteroarylalkyl" defines a subset of "heteroaryl" wherein an alkyl group, as defined herein, links the heteroaryl group to the parent molecule.

As used herein, the term "substituted heteroaryl" refers to heteroaryl as just described wherein the heteroaryl nucleus is substituted with one or more functional groups such as lower alkyl, halo, haloalkyl (e.g. $CF_3$), hydroxy, amino, alkoxy, alkylamino, acylamino, thio, alkylthio, etc.

As used herein, the term "substituted heterocyclic" describes a heterocyclic group, wherein the heterocycle nucleus is substituted with one or more functional groups such as lower alkyl, halo, haloalkyl (e.g. $CF_3$), hydroxy, amino, alkoxy, alkylamino, acylamino, thio, alkylthio, etc.

As used herein, the term "aralkyl" means one or more hydrogens on an alkyl groups are substituted by an aryl group (e.g., an aromatic or heteroaromatic group). The alkyl can be, for example, a lower alkyl. Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. alkyl groups are lower alkyls. In embodiments, a substituent designated herein as alkyl is a lower alkyl.

As used herein, the term "substituted" means any of the above groups (for example, alkyl, alenyl, alkynyl, cycloalkyl and aryl) wherein at least one hydrogen atom is replaced with a substituent. The term "substituted" as used herein means any of the above groups (e.g., alkyl, aryl, aralkyl, heteroaryl, heteroaralkyl, heterocyclyl and heterocyclylalkyl) wherein at least one hydrogen atom is replaced with a substituent. When substituted, "substituents" within the context of this invention include halo, haloalkyl, hydroxy, amino, alkylamino, dialkylamino, guanidine, ureido, thio, alkyl, alkoxy, alkylthio, aryl, substituted aryl, aralkyl, substituted aralkyl, heteroaryl, substituted heteroaryl, heteroaralkyl, substituted heteroaralkyl, heterocyclyl, substituted heterocyclyl, heterocyclylalkyl, or substituted heterocyclylalkyl.

As used herein, the term "halo" means fluoro, chloro, bromo and iodo.

As used herein, the term "haloalkyl" means an alkyl having at least one hydrogen atom replaced with halogen, such as trifluoromethyl and the like.

As used herein, the term "alkoxy" means an alkyl moiety attached through an oxygen bridge (i.e., —O-alkyl, —O-alkenyl, —O-alkynyl, —O-cycloalkyl) such as methoxy, ethoxy, 2-propenyloxy, 2-propynyloxy, cyclohexyloxy and the like.

As used herein, the term "aryloxy" means an aryl moiety attached through an oxygen bridge (i.e., —O-aryl) such as phenoxy.

As used herein, the term "aralkyloxy" means an aralkyl moiety attached through an oxygen bridge (i.e., —O-aralkyl) such as benzyloxy.

As used herein, the term "alkylthio" means a hydrocarbyl moiety attached through a sulfur bridge (i.e., —S-alkyl, —S-alkenyl, —S-alkynyl or —S-cyclohexyl) such as methylthio, ethylthio, and the like.

As used herein, the term "amino" means $NH_2$ group or wherein a hydrogen atom is substituted by an imino-aminomethyl or carboxamido group, such as guanidine and ureido.

As used herein, the term "alkylamino" means an amino (—NH$_2$) group in which one or more of the hydrogen atoms can be further replaced by "hydrocarbyl" group such as ethylamino, diethylamino, pyrrolidino, and the like As used herein, the term "aminoalkyl" means a hydrocarbyl, such as alkyl, group in which one or more of the hydrogen atoms can be further replaced by an "amino" group such as aminomethyl-(imino)propyl i.e. guanidine and the like As used herein, the term "aralkylamino" means an amino (—NH$_2$) group in which one or more of the hydrogen atoms can be further replaced by an aralkyl group, such as benzyl (phenylmethyl).

As used herein, the term "Hydroxyalkyl" means an alkyl in which a hydrogen is substituted with a hydroxy group.

As used herein, the term "acyloxy" represents an alkyl-C(=O)— group, such as acetyl.

As used herein, the term "alkyloxycarbonyl" represents a —C(=O)Oalkyl group, such as a ethoxycarbonyl (—COOEt) group.

As used herein, the term "alkyloxyalkyl" in general means substitution of a hydrogen atom of a hydrocarbyl group with a —O-hydrocarbyl group, such as ethoxyethyl.

As used herein, "alkylthioalkyl" means substitution of a hydrogen atom of a hydrocarbyl group with a —S-hydrocarbyl group, such as methylthiomethyl.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline and γ-carboxyglutamate. Amino acid analogs refers to compounds that have the same basic chemical structure as a naturally occurring amino acid, i.e. an α-carbon that is bound to a hydrogen, a carboxyl group, an amino group, and an R group, e.g., homoserine, norleucine, norvaline, which have modified R groups (e.g., norvaline), but retain the same basic chemical structure as a naturally occurring amino acid. Amino acid mimetics refers to chemical compounds that have a structure that is different from the general chemical structure of an amino acid, but that functions in a manner similar to a naturally occurring amino acid, such as β-alanine or γ-aminobutyric acid.

The abbreviations Me, Et, Ph, Bzl, Tf, Ts, TFA, HF, HOBt, DIEA, DICI, Cbz, Fmoc and Boc represent methyl, ethyl, phenyl, benzyl, trifluoromethanesulfonyl, p-toluenesulfonyl, trifluoroacetic acid, hydrofluoric acid, 1-Hydroxybenzotriazole, N,N-Diisopropylethylamine, 1,3-Diisopropylcarbodiimide, benzyloxycarbonyl, 9-fluorenylmethyloxycarbonyl and t-butyloxycarbonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

An MCH receptor antagonist can be selective for a particular MCH receptor, such as MCH1R. For example, TPI 1361-17 was demonstrated to antagonize MCH1R but to not appreciably antagonize MCH2R. As such, a "selective" MCH1R antagonist is a compound that reduces MCH1R activity at least 10-fold more than any reduction affected by the antagonist on another MCH receptor form, such as MCH2R. A selective MCH receptor antagonist can have, for example, at least 10-fold selectivity for MCH1R relative to MCH2R, at least 20-fold, at least 40-fold, at least 80-fold, at least 100-fold, at least 500-fold, at least 800-fold, or at least 1000-fold selectivity for MCH1R relative to MCH2R.

An MCH receptor antagonist of the invention can act by any mechanism, such as by binding the MCH receptor or a ligand therefore, thereby inhibiting binding between receptor and ligand. An MCH receptor antagonist can also inhibit binding between a specific or non-specific agonist and MCH receptor. An MCH receptor antagonist can also act, for example, by inhibiting the binding activity of a ligand or signaling activity of the MCH receptor. An MCH receptor antagonist can also be an inverse agonist, which decreases MCH receptor signaling from a baseline amount of constitutive signaling activity.

The compounds of the invention can be synthesized by applying the general synthetic methodology described below in Example V, and in Nefzi et al. Tetrahedron Letters, 38:931-934 (1997), and by such modifications of the hereinafter described specific synthetic routes which will become readily apparent to the practicing synthetic organic chemist in light of this disclosure and in view of general knowledge available in the art. The hereinafter disclosed specific reaction schemes are directed to the synthesis of exemplary and compounds of the invention. Whereas each of the specific and exemplary synthetic routes shown in these schemes can describe specific compounds of the invention only within the scope of one or two of the general formulas, the synthetic processes and methods used therein are adaptable within the skill of the practicing organic chemist and can be used with such adaptation for the synthesis of compounds of the invention which are not specifically described herein as examples.

The compounds of the invention can be used in the form of acid addition salts or free bases. Acid addition salts of the free base amino compounds of the present invention can be prepared by methods well known in the art, and can be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" encompasses any and all acceptable salt forms.

In addition, prodrugs are also included within the context of this invention. Prodrugs are any covalently bonded carriers that release a compound of formula I in vivo when such prodrug is administered to an individual. Prodrugs are generally prepared by modifying functional groups in a way such that the modification is cleaved, either by routine manipulation or in vivo, yielding the parent compound.

With regard to stereoisomers, the compounds of formula I can have chiral centers and occur as racemates, racemic mixtures and as individual enantiomers or diastereomers. All such isomeric forms are included within the present invention, including mixtures thereof. Furthermore, some of the crystalline forms of the compounds of formula I can exist as polymorphs, which are included in the present invention. In addition, some of the compounds of formula I can also form solvates with water or other organic solvents. Such solvates are similarly included within the scope of this invention.

A compound of formula I can be labeled with a radioisotope, such as $^{11}$C, $^{125}$I, $^{35}$S, $^{3}$H, $^{18}$F and the like. A radiolabelled compound of the invention can be used, for example, in an imaging method, such as Positron Emission Tomography (PET), Single Photon Emission Computed Tomography (SPECT), or in other diagnostic methods. Incorporation of an appropriate isotope (such as $^{11}$C or $^{18}$F for PET or $^{125}$I for SPECT) can be performed using well known synthetic methods. When used in such a diagnostic method, a radiolabelled compound of the present invention can provide a physiological, functional, or biological assessment of an individual or provide disease or pathology detection and assessment.

The ability of a compound to antagonist MCH receptor can be determined using any of a variety of assays. Such assays can be performed, for example, in a cell or tissue that expresses endogenous or recombinant MCH receptor, and generally involve determining MCH receptor activity or a downstream effect of MCH receptor activity prior to and following application of a test compound. A downstream effect of MCH receptor activity activity can be, without limitation, a change in intracellular calcium mobilization, arachidonic acid release and the like. Methods for measuring MCH receptor activity are well known to those skilled in the art, and are described, for example, in Wang et al. J. Biol. Chem., 276:34664-34670, (2001), as well as in Examples I to III.

A variety of cell types, including naturally occurring and genetically engineered cells, can be used in an in vitro assay to detect MCH receptor activity or a downstream effect of MCH receptor activity. Genetically engineered cells expressing MCH receptor are described, for example, in Examples I-III. Naturally occurring cells that express endogenous MCH receptor include, for example, cells obtained from an organ that expresses MCH receptor, such as brain tissues, pituitary, normal portions of adrenal glands (cortex and medulla), tumor tissues of adrenocortical tumors, pheochromocytoma, ganglioneuroblastoma, neuroblastoma, as well as in several cell lines, as is described in Takahashi et al. J Clinical Endocrinology & Metabolism 86:369-374. Other naturally occurring cells and cell lines that express MCH receptor can be identified by those skilled in the art using methods disclosed herein and other methods well known in the art. Cells for use in testing a compound for its ability to antagonize MCH receptor can be obtained from an mammal, such as a mouse, rat, pig, goat, primate or human, or a non-mammal.

Cells expressing MCH receptor can be prepared using a variety of methods. Recombinant expression can be advantageous in providing a higher level of expression of MCH receptor than is found endogenously, and also allows expression in cells or extracts in which expression is not normally found. A recombinant nucleic acid expression construct generally contains a constitutive or inducible promoter of RNA transcription appropriate for the host cell or transcription-translation system, operatively linked to a nucleotide sequence that encodes a polypeptide corresponding MCH receptor or an active fragment thereof. The expression construct can be DNA or RNA, and optionally can be contained in a vector, such as a plasmid or viral vector.

The nucleotide and amino acid sequences of human MCH receptor is available to one skilled in the art, for example, under GenBank Accession No NM_005297. Other human MCH receptor nucleotide and polypeptide sequences are available from GenBank, as are othologous MCH receptor sequences from rat (AF008650), mouse and other species. Any of these MCH receptor nucleotide sequences can be used to recombinantly express an MCH receptor in an assay for confirming the activity of an MCH receptor antagonist. One skilled in the art can recombinantly express desired levels of MCH receptor using routine laboratory methods, described, for example, in standard molecular biology technical manuals, such as Sambrook et al., Molecular Cloning: A Laboratory Manual, Cold Spring Harbor Laboratory, New York (1992) and Ansubel et al., Current Protocols in Molecular Biology, John Wiley and Sons, Baltimore, Md. (1998).

The MCH receptor antagonists of the invention can be used to beneficially modulate MCH receptor activity to treat an individual having a condition associated with MCH receptor. As used herein, a "condition associated with MCH receptor" means any disease or condition in which modulation of the activity of MCH receptor can be beneficial. It is understood that the underlying cause of the disease can or can not be due to an abnormality in expression or activity of MCH receptor.

Compounds that antagonist the MCH receptor can be useful in regulating MCH-mediated biological responses involving food intake, adipocyte function, and energy metabolism, which in turn can beneficially reduce symptoms of individuals having a variety of conditions associated with excessive or insufficient food intake, adipocyte function or energy metabolism. Such conditions include, for example, eating or feeding disorders, obesity, and metabolic disorders, such as diabetes. Therefore, such antagonists can be used to beneficially treat an obese individual, or one at risk of becoming obese.

Accordingly, the invention provides a method of prophylactic therapy for obesity. The method is practiced by administering to a non-obese or pre-obese individual an effective amount of a compound of the invention, in order to reduce development of obesity. As used herein, the term "non-obese" refers to a body mass index (BMI) of less than 25 $kg/m^2$, whereas the term "pre-obese" refers to a BMI of at least 25 $kg/m^2$ and less than 27 $kg/m^2$. Body mass index is a measure of an individual's weight in kilograms divided by the square of the individual's height in meters.

In another embodiment, the invention provides a method of therapy for obesity. The method is practiced by administering to an obese individual an effective amount of a compound of the invention. As used herein, the term "obese" refers to an individual having a BMI of at least 27 $kg/m^2$, such as a BMI of at least 28, 29, or 30 $kg/m^2$.

From an analysis of mortality data in 1.4 million individuals, the risk of death was shown to rise sharply with BMI>27 kg/m2 (Calle et al., N. Engl. J. Med. 341:1097-1105 (1999)). Therefore, the methods of the invention, by preventing or reducing obesity, can advantageously also reduce mortality associated with obesity.

Additional non-limiting examples of conditions associated with MCH receptor include psychiatric disorders, such as depression, and muscle control disorders, such as urinary incontinence.

As used herein, the terms "treating" or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the individual, which provides the desired effect in the individual under diagnosis or treatment. The dose regimen will depend on a number of factors which can readily be determined, such as severity and responsiveness of the condition to be treated, but will normally be one or more doses per day, with a course of treatment lasting from several days to several months, or until a cure is effected or a diminution of disease state is achieved. One of ordinary skill can readily determine optimum dosages, dosing methodologies and repetition rates. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the migraine involved; the response of the individual; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. For example, a daily doses can be about 0.05 mg/kg to about 50 mg/kg, such as from about 0.1 mg/kg to about 25 mg/kg. Topical formulations (such as creams, lotions, solutions, etc.) can have a concentration of active ingredient of from about 0.1% to about 50%, preferably from about 0.1% to about 10%. However, final strength of the finished dosage form will depend on the factors listed above and can be readily determined by one of ordinary skill.

For treating a condition associated with MCH receptor, more than one therapeutic approach or compound can be provided to an individual for maximal symptom control. Thus, a compound of the invention can advantageously be administered concurrently or sequentially with another therapeutic mode or formulated with a second compound that controls the same or related symptoms. For example, in treating obesity, a compound of the invention can be administered while an individual is receiving another treatment for obesity.

A compound of the invention therefore can be administered alone, in combination with, or in sequence with, other compounds or modalities. The skilled clinician will be able to determine concurrent or sequential therapies appropriate for use with a compound of the invention. Methods of drug therapy for obesity, and strategies for developing additional drug therapies, are known in the art (see, for example, Bray et al., Nature 404: 672-677 (2000)). Exemplary drug therapies for obesity can advantageously involve one or more of the following strategies:

1) Reducing food intake, either by amplifying signals or factors that suppress food intake, or blocking signals that stimulate food intake. An exemplary therapeutic compound that acts by this mechanism is Sibutramine (sold under the trademarks Meridia and Reductil), which inhibits the reuptake of noradrenaline, serotonin and dopamine. Other exemplary therapeutics for reducing food intake can target central neuropeptide or monoamine systems such as the leptin system, melanocortin receptor system, melanin concentrating receptor system, opioid receptor system, neuropeptide Y receptor system, and histaminergic receptor system, or can target peripheral gastrointestinal or pancreatic peptide systems (e.g. cholecystokinin, gastrin-releasing peptide, neuromedin, bombesin, glucagon, enterostatin, amylin, and nutrients and their analogs).

2) Blocking absorption of nutrients, and particularly fat, in the gut. An exemplary therapeutic compound that acts by this mechanism is Orlistat (sold under the trademark Xenical), which blocks pancreatic lipase, thereby decreasing triglyceride digestion.

3) Increasing thermogenesis, by uncoupling fuel metabolism from generation of ATP, thereby dissipating food energy as heat. Exemplary therapeutic compounds that act at least in part by this mechanism include ephedrine and caffeine.

4) Modulating fat or protein metabolism or storage, by regulating fat synthesis/lipolysis or adipose differentiation/apoptosis. Enhanced fat or protein turnover can affect food intake or energy expenditure or both.

5) Modulating the central controller regulating body weight. This can be accomplished either by altering the internal reference value sought by the controller, or by modulating the primary afferent signals regarding fat stores that are analyzed by the controller.

For therapeutic or prophylactic treatment, the compounds of the present invention can be formulated in a pharmaceutical composition, which can include, in addition to an effective amount of active ingredient, pharmaceutically acceptable carriers, thickeners, diluents, buffers, preservatives, surface active agents and the like. Suitable pharmaceutically acceptable carriers are well known in the art and include, for example, aqueous or organic solvents such as physiologically buffered saline, glycols, glycerol, oils or injectable organic esters. A pharmaceutically acceptable carrier can also contain a physiologically acceptable agent that acts, for example, to stabilize or increase solubility of a pharmaceutical composition. Such a physiologically acceptable agent can be, for example, a carbohydrate such as glucose, sucrose (Not in obesity treatment—lactose can be better or xylitol, sorbitol, mannitol are much) or dextrans; an antioxidant such as ascorbic acid, tocopherols or glutathione; a chelating agent; a low molecular weight polypeptide; or another stabilizer or excipient. Pharmaceutically acceptable carriers including solvents, stabilizers, solubilizers and preservatives, are well known in the art as described, for example, in Martin, Remington's Pharmaceuitical Sciences, 18th Ed; Mack publishing company, Easton, Pa., 1990. Pharmaceutical compositions can also include one or more other active ingredients if necessary or desirable.

The pharmaceutical compositions of the present invention can be administered in a number of ways as will be apparent to one of ordinary skill. Administration can be done topically, orally, rectally, nasally, sublingually, buccally, vaginally, by inhalation, or parenterally (including subcutaneous, intramuscular, intravenous and intradermal), for example.

Topical formulations can include ointments, lotions, creams, gels, drops, suppositories, sprays, liquids and powders. Oral formulations include powders, granules, suspensions or solutions in water or non-aqueous media, capsules or tablets, for example. Thickeners, flavorings, diluents, emulsifiers, dispersing aids or binders can be used as needed.

Parenteral formulations can include sterile aqueous solutions, which can also contain buffers, diluents and other suitable additives.

Methods of ensuring appropriate distribution in vivo also can be provided by rechargeable or biodegradable devices, particularly where concentration gradients or continuous delivery is desired. Various slow release polymeric devices are known in the art for the controlled delivery of drugs, and include both biodegradable and non-degradable polymers and hydrogels. Polymeric device inserts can allow for accurate dosing, reduced systemic absorption and in some cases, better individual compliance resulting from a reduced frequency of administration. Those skilled in the art understand that the choice of the pharmaceutical formulation and the appropriate preparation of the compound will depend on the intended use and mode of administration.

An effective amount of a compound of the invention can be administered to a individual by any of a variety of means depending, for example, on the type of condition to be treated, the pharmaceutical formulation, and the history, risk factors and symptoms of the individual. Routes of peripheral administration suitable for the methods of the invention include both systemic and local administration. As non-limiting examples, an effective amount of a compound of the invention can be administered orally; sublingually; parenterally; by subcutaneous pump; by dermal patch; by intravenous, intraarticular, subcutaneous or intramuscular injection; by topical drops, creams, gels or ointments; as an implanted or injected extended release formulation; or by subcutaneous minipump or other implanted device, and by inhalation by aerosol and similar devices.

One skilled in the art understands that peripheral administration can be local or systemic. Local administration results in significantly more of a compound of the invention being delivered to and about the site of local administration than to regions distal to the site of administration. Systemic administration results in delivery of a compound of the invention essentially throughout at least the entire peripheral system of the individual.

Routes of peripheral administration useful in the methods of the invention encompass, without limitation, oral administration, sublingual administration, topical administration, intravenous or other injection, and implanted minipumps or other extended release devices or formulations. A compound of the invention can be peripherally administered, without limitation, orally in any acceptable form such as in a tablet, pill, capsule, powder, liquid, suspension, emulsion or the like; as an aerosol; as a suppository; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation. A compound of the invention optionally can be packaged in unit dosage form suitable for single administration of precise dosages, or in sustained release dosage form for continuous controlled administration.

An effective dose of a compound of the invention can be determined, for example, by extrapolation from the concentration required in an animal model, such as one of the in vivo assays disclosed herein above. An effective dose of a compound also can be determined from appropriate animal models. An effective dose for preventing or reducing the severity of a condition is a dose that results in either partial or complete alleviation of at least one symptom of the condition. The appropriate dose of a compound for treatment of a human individual can be determined by those skilled in the art, and is dependent, for example, on the particular disease being treated and its severity, the nature and bioactivity of the particular compound, the desired route of administration, the gender, age and general health of the individual, and the number of doses and duration of treatment.

It is understood that modifications which do not substantially affect the activity of the various embodiments of this invention are also included within the definition of the invention provided herein. Accordingly, the following examples are intended to illustrate but not limit the present invention.

EXAMPLE I

Screening of Positional Scanning Synthetic Combinatorial Libraries (PS-SCL)

This Example shows screening for an MCH receptor antagonist using positional scanning synthetic combinatorial libraries (PS-SCL).

Several heterocyclic and peptidomimetic positional scanning combinatorial libraries (PS-SCL) were used for screening. Each library was prepared by using simultaneous multiple synthesis technology (Houghten, 1985, Nefzi et al. Tetrahedron Letters 38:931-934 (1997)) as described elsewhere (Ostresh, 1998). A list of the libraries and a representation of an N-benzyl aminocyclic thiourea is presented in Table 1. The identity and purity of each individual compound were analyzed by mass spectral analysis interfaced with a liquid-chromatography system (Finnigan LCQ) and/or analytical reverse-phase high performance liquid chromatography (RP-HPLC) using a Vydac C18 column and a Beckman system Gold HPLC. The compounds were purified by using a Waters Milliprep 3400 preparative HPLC with a preparative Foxy fraction collector.

A total of thirteen heterocyclic or peptidomimetics PS-SCLs containing 8,136,870 individual compounds were tested (Table 1). Most libraries were generated in a PS format by using 40~50 amino acids at each of the $R_1$ and $R_2$ positions, and 40~80 carboxylic acids at the $R_3$ position. A sample set of PS-SCLs was screened initially, sub-libraries with defined $R_3$ positions and a mixture of building blocks at each of the other two positions were prepared (all compounds in the library are represented). Each sub-library was composed of 40~80 mixtures containing 1,500~3,200 individual compounds. A total of 618 separate mixtures were screened for inhibition of 30 nM MCH-induced $Ca^{2+}$ mobilization in CHO cells expressing MCH1R. Mixtures showing $IC_{50}$ values lower than 2.5 □g/ml were considered bioactive. The N-benzyl aminocyclic thiourea PS-SCL exhibited 26 hits out of 80 sub-libraries, while the N-methyl aminocyclic thiourea PS-SCL had one out of 80. There were no agonistic or MCH1R antagonistic activities in the other libraries.

TABLE 1

PS-SCLs tested for MCH1R antagonism.

| Templates | Diversity (# of total cpds.) | # of active mixture/ # of total mixture |
|---|---|---|
| Heterocycles | | |
| N-benzylamino cyclic thioureas | 118,400 | 26/80 |
| N-methylamino cyclic thioureas | 118,400 | 1/80 |
| N-methyl diketopiperazines | 31,320 | 0/40 |
| N-benzyl diketopiperazines | 31,320 | 0/40 |
| N-methyl piperazines | 31,320 | 0/40 |
| N-benzyl piperidines | 31,320 | 0/40 |
| C-6-acylamino bicyclic guanidines | 72,283 | 0/40 |
| bicyclic guanidines | 102,459 | 0/88 |
| bis-diketopiperazines | 45,864 | 0/40 |
| Peptidemimetics | | |
| triphenylureas | 85,248 | 0/40 |
| N-acyl triamines | 125,000 | 0/50 |
| N-methyltriamines | 31,320 | 0/40 |
| N-per-methylated PENTAMINES | 7,311,616 | 0/104 |

EXAMPLE II

Screening of N-benzylamino Cyclic Thiourea PS-SCL

This Example shows screening for an MCH receptor antagonist using an N-benzyl-amino cyclic thiourea PS-SCL.

The N-benzylamino cyclic thiourea PS-SCL was subjected to further deconvolution. This library had been generated in a PS format by using 40 amino acids at $R_1$ Position, 37 amino acids at the $R_2$ position, and 80 carboxylic acids at the $R_3$ position for a total of 118,400 (40×37×80) individual compounds (FIG. 1A). The complete PS-SCL was composed of three sub-libraries, each of which had a single defined building block at one position and a mixture of building blocks at each of the other two positions (Table 2). Each sub-library contained the same number of compounds (118,400). Pooling of each sub-library varied based on the number of building blocks included at the defined position of that sub-library. The PS-SCL was composed of 157 separate mixtures (i.e., 40+37+80=157 samples to be assayed), each mixture contained from 1,480 (40×37) to 3,200 (40×80) individual compounds, depending on the location of the defined position. The structure(s) of the active individual compound(s) present in the library can be directly determined from the screening of these 157 mixtures, since each individual compound is present in a single mixture in each of the three sub-libraries.

TABLE 2

Building blocks used in the N-benzyl thiourea PS-SCL

Building block

| No. | $R_1$ | $R_2$ | $R_3$ |
|---|---|---|---|
| 1 | L-Ala | L-Ala | 1-Phenyl-1-cyclopropanecarboxylic acid |
| 2 | L-Phe | L-Phe | 2-Phenylbutyric acid |
| 3 | L-Gly | Gly | 3-Phenylbutyric acid |
| 4 | L-Ile | L-Ile | 3-methylphenyl acetic acid (m-Tolylacetic acid) |
| 5 | L-Lys(Boc) | L-Leu | 3-Fluorophenylacetic acid |
| 6 | L-Leu | L-Met(O) | 3-Bromophenylacetic acid |
| 7 | L-Met(O) | L-Arg(Pmc) | (□-□-□-Trifluoro-m-tolyl)acetic acid |
| 8 | L-Asn | L-Ser(tBu) | 4-methylphenyl acetic acid (p-Tolylacetic acid) |
| 9 | L-Gln | L-Thr(tBu) | 4-Fluorophenylacetic acid |
| 10 | L-Arg(Pmc) | L-Val | 3-Methoxyphenylacetic acid |
| 11 | L-Ser(tBu) | L-Trp(Boc) | 4-Bromophenylacetic acid |
| 12 | L-Thr(tBu) | L-Tyr(BrZ) | 4-Methoxyphenylacetic acid |
| 13 | L-Val | L-Tyr(tBu) | 4-Ethoxyphenylacetic acid |
| 14 | L-Trp | D-Ala | 4-Isobutyl-□-methylphenylacetic acid |
| 15 | L-Tyr(BrZ) | D-Phe | 3,4-Dichlorophenylacetic acid |
| 16 | L-Tyr(tBu) | D-Ile | 3,5-bis-(Trifluoromethyl)phenyl-acetic acid |
| 17 | D-Ala | D-Leu | 3-(3,4-Dimethoxyphenyl)propionic acid |
| 18 | D-Phe | D-Ser | 4-Biphenylylacetic acid |
| 19 | D-Ile | D-Thr(tBu) | □-Methylcinnamic acid |
| 20 | D-Lys(Boc) | D-Val | 2-(Trifluoromethyl)cinnamic acid |
| 21 | D-Leu | D-Trp(Boc) | (3,4-Dimethoxyphenyl)acetic acid |
| 22 | D-Asn | D-Tyr(tBu) | 3,4-(Methylenedioxy)phenylacetic acid |
| 23 | D-Gln | D-Arg(Pmc) | 2-Methoxycinnamic acid |
| 24 | D-Ser | L-Nle | Benzoic acid |
| 25 | D-Thr(tBu) | D-Nle | 4-Chlorocinnamic acid |
| 26 | D-Val | L-Nva | trans-Cinnamic acid |
| 27 | D-Trp | D-Nva | 3-methylphenyl acetic acid (m-Toluic acid) |
| 28 | D-Tyr(tBu) | L-NapAla | Phenylacetic acid |
| 29 | D-Arg(Pmc) | D-NapAla | Hydrocinnamic acid |
| 30 | L-Nle | L-Phg | 4-Phenylbutyric acid |
| 31 | D-Nle | L-Glu(tBu) | 3,5-bis-(Trifluoromethyl)benzoic acid |
| 32 | L-Nva | D-Glu(tBu) | Butyric acid |
| 33 | D-Nva | □Ala | Heptanoic acid |
| 34 | L-NapAla | L-ChAla | Isobutyric acid |
| 35 | D-NapAla | D-ChAla | (+/−)-2-Methylbutyric acid |
| 36 | L-Phg | L-His(Trt) | Isovaleric acid |
| 37 | L-ChAla | D-His(Trt) | 3-Methylvaleric acid |
| 38 | D-ChAla | | 4-Methylvaleric acid |
| 39 | L-His(Trt) | | Crotonic acid |
| 40 | D-His(Trt) | | Vinylacetic acid |
| 41 | | | 4-methylphenyl acetic acid (p-Toluic acid) |
| 42 | | | Trimethylacetic acid |
| 43 | | | tert-Butylacetic acid |
| 44 | | | Cyclohexanecarboxylic acid |
| 45 | | | Cyclohexylacetic acid |
| 46 | | | Cyclohexylbutyric acid |
| 47 | | | Cycloheptanecarboxylic acid |

TABLE 2-continued

Building blocks used in the N-benzyl thiourea PS-SCL

Building block

| No. | $R_1$ | $R_2$ | $R_3$ |
|---|---|---|---|
| 48 | | | Acetic acid |
| 49 | | | 2-Methylcyclopropane-carboxylic acid |
| 50 | | | Cyclobutanecarboxylic acid |
| 51 | | | Cyclopentanecarboxylic acid |
| 52 | | | 3-Cyclopentylpropionic acid |
| 53 | | | Cyclohexanepropionic acid |
| 54 | | | 4-Methyl-1-cyclohexane-carboxylic acid |
| 55 | | | 4-tert-Butyl-cyclohexane-carboxylic acid |
| 56 | | | 4-Methylcyclohexylacetic acid |
| 57 | | | Tiglic acid |
| 58 | | | 1-Adamantaneacetic acid |
| 59 | | | Niflumic acid |
| 60 | | | 4-Nitrophenylacetic acid |
| 61 | | | 4-(Nitrophenyl)-butyric acid |
| 62 | | | 4-Nitrocinnamic acid |
| 63 | | | 2-Nitrobenzoic acid |
| 64 | | | 2,4-Dinitrophenyl acetic acid |
| 65 | | | 4-Biphenylacetic acid |
| 66 | | | 2-Chloro-5-nitrobenzoic acid |
| 67 | | | (4-Pyridylthio)acetic acid |
| 68 | | | 3-3 Diphenylpropionic acid |
| 69 | | | 2-Chloro-4-nitrobenzoic acid |
| 70 | | | 4-Dimethylaminobenzoic acid |
| 71 | | | 4-Nitrobenzoic acid |
| 72 | | | 3-Dimethylaminobenzoic acid |
| 73 | | | Abietic acid |
| 74 | | | 2-Methyl-4-nitro-1-imidazole-propionic acid |
| 75 | | | trans-Styrylacetic acid |
| 76 | | | Cyclopentylacetic acid |
| 77 | | | Dicyclohexylacetic acid |
| 78 | | | (2-Pyridylthio)acetic acid |
| 79 | | | Pentadienoic acid |
| 80 | | | Indole-3-acetic acid |

Each mixture was assayed in duplicate in three separate assays at three concentrations (1, 0.1 and 0.01 □g/ml) (FIG. 1B). MCH1R inhibition was calculated as the percent decrease in intracellular $Ca^{2+}$ mobilization in MCH1R expressing CHO cells induced by 30 nM MCH in the presence or absence of the mixture. None of the 157 mixtures elicited increases in $Ca^{2+}$ mobilization alone. Mixtures showing highest reproducible antagonism and dose-dependency were selected for deconvolution. A set of 84 individual N-benzylamino cyclic thioureas was then generated to confirm the connectivity between the selected building blocks (i.e., if the activities of the selected mixtures are due to the same individual compounds), as well as to determine the relative activities of the individual compounds. Each compound was assayed at five different concentrations derived from serial ten-fold dilutions starting at 10 □M (FIG. 2A). The lowest $IC_{50}$ values were in the nM range, found with the combination of L-Alanine at $R_1$ position, L-Arginine at $R_2$, and phenylacetic acids at $R_3$. The compound with the highest affinity, TPI 1361-17 (N-(3-{(4S)-1-[(1S)-2-(benzylamino)-1-methylethyl]-3-[2-(3-fluorophenyl)ethyl]-2-thioxoimidazolidin-4-yl}propyl)guanidine, (FIG. 2B) was selected for further pharmacological analyses. By mass spectrometry, the molecular weight of purified TPI 1361-17 was 470.26, which matched exactly the one expected.

HEK293T cells expressing the rat MCH1R were scraped with ice-cold PBS and centrifuged at 1000×g for 5 min. Cell pellet was homogenized with ice-cold 50 mM Tris-HCl buffer (pH 7.4) containing 5 mM EDTA, and ultra-centrifuged twice at 48,000×g for 20 min at 4° C. The pellets were then suspended in 50 mM Tris-HCl (pH 7.4) buffer containing 5 mM EDTA and used as membrane fractions. The membrane fraction (30 µg protein for each assay) dissolved in 500 µl assay buffer containing 50 mM Tris-HCl buffer (pH 7.4), 1 µM phosphoramidon, 0.5 mM phenylmethylsulfonylfluoride and 0.2% BSA with 0.1 nM [$^{125}$I] (Phe13, Tyr19) MCH and various concentrations of cold MCH and TPI1361-17 at room temperature for 2 h. Nonspecific binding was determined by including 1 µM MCH in the binding reaction. The binding reaction was terminated by rapid filtration through GF/C filter plates pre-soaked in 0.2% polyethylenimine, followed by washing three times with 3 ml of PBS. The radioactivity retained in the filters was determined with a γ-counter. $IC_{50}$ values calculated as described above are expressed as the mean +S.E.M. for three independent determinations.

DNA was mixed with LipofectAMINE transfection reagents (Life Technologies, MD), and the mixture was diluted with Opti-MEM and added to 60-70% confluent HEK 293T cells plated on 100-mm dishes. The transfected cells were cultured in DMEM containing 10% FBS. For Calcium mobilization assay (see Example III) and radioligand binding assay, CHO cells or HEK-293T cells stably expressing rat MCH1R were used (Saito et al., 1999).

EXAMPLE III

Cellular Effects of Antagonism of MCH Receptor by a N-benzylamino Cyclic Thiourea This example shows the ability of TPI 1361-17 to antagonize MCH1R in cells.

Figure 3:
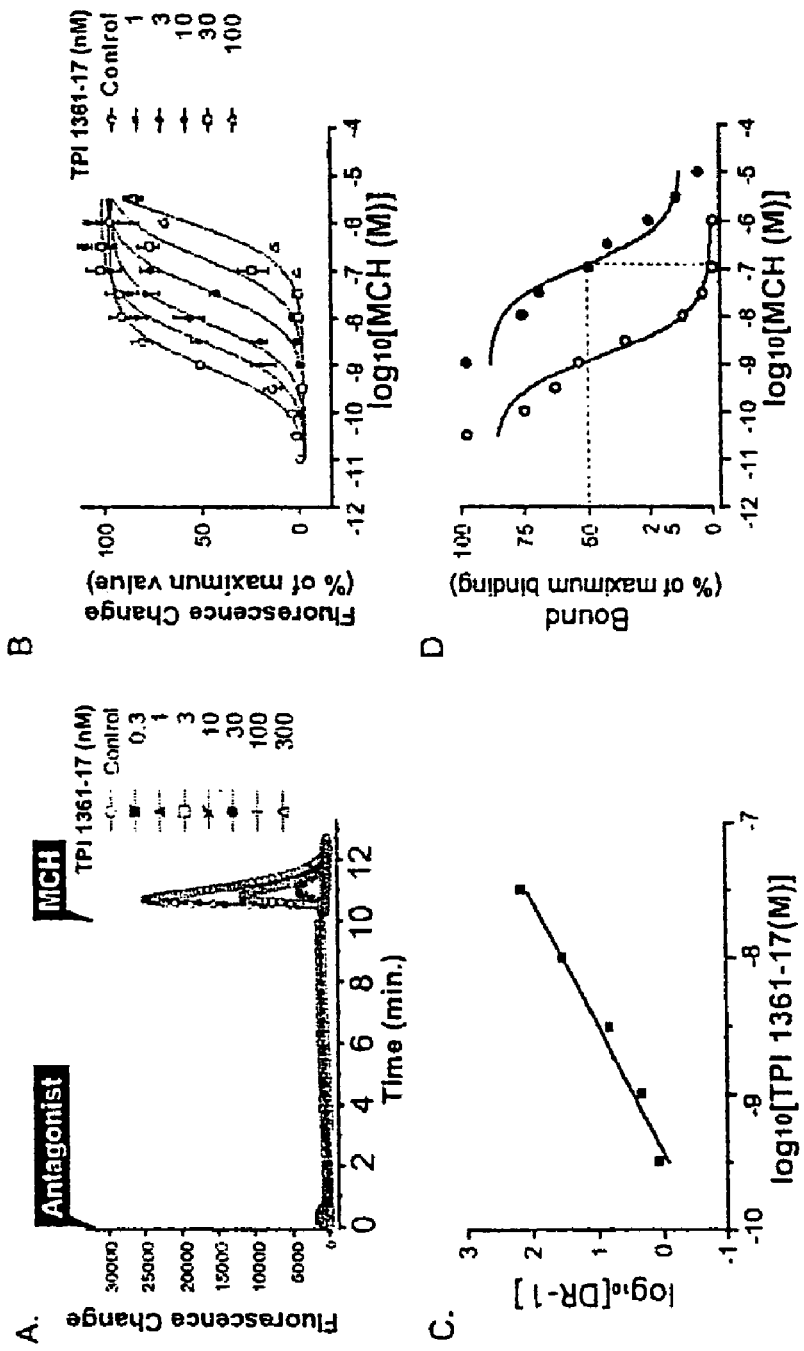
FIG. 3 shows in vitro pharmacology of TPI 1361-17 (Formula IV).

MCH stimulated the $Ca^{2+}$ mobilization in HEK 293T cell expressing rat MCH1R with an EC50 value of 0.9 nM (FIG. 3A). TPI 1361-17 showed $IC_{50}$ value of 6.1 nM on 1 nM MCH-induced $Ca^{2+}$ mobilization. TPI 1361-17 did not change the basal $Ca^{2+}$ level by itself, but significantly inhibited the MCH-induced $Ca^{2+}$ mobilization. The addition of increasing concentrations of TPI 1361-17 caused a progressive shift of the curve to the right. The Schild regression estimated a pA2 of 9.43 with a slope of 1.085±0.010 (r2=0.975), which predicts a Kb of 0.37 nM (FIGS. 3B, 3C). This compound was more than 1,000 fold selective for MCH1R compared with the human MCH2R, as well as GPCRs including neuropeptide Y2, orexin 1R, prolactin releasing peptide (PrRP) receptor, and kappa opioid receptor (dynorphin). TPI 1361-17 also exhibited a high affinity for rat MCH1R in binding assays. TPI 1361-17 completely displaced the binding of [125I] MCH to rat MCH1R, with an $IC_{50}$ value of 140.3±34.6 nM (mean ±S.E.M.) (FIG. 3D).

Transfected HEK293T cells seeded on black-walled 96-well plates (Sigma, St Louis USA) were loaded for 1 h at 37° C. with $Ca^{2+}$-sensitive fluorescent dye, fluo-4 (Molecular Device, CA) in Hanks' balanced salt solution containing 20 mM HEPES (pH 7.4). The level of $[Ca^{2+}]i$ was then monitored using a FLIPR system (Fluorometric Imaging Plate Reader; Molecular Devices, San Francisco, Calif.). For antagonists screening, each mixture from the compound library was first incubated with the cell for 10 minutes, before the addition of MCH. Data were expressed as fluorescence (arbitrary units) versus time.

EXAMPLE IV

In Vivo Effects of Antagonism of MCH Receptor by a N-benzylamino Cyclic Thiourea This example describes that administration of benzylamino cyclic thiourea TPI 1361-17 to rats results in reduced food intake.

Figure 4:
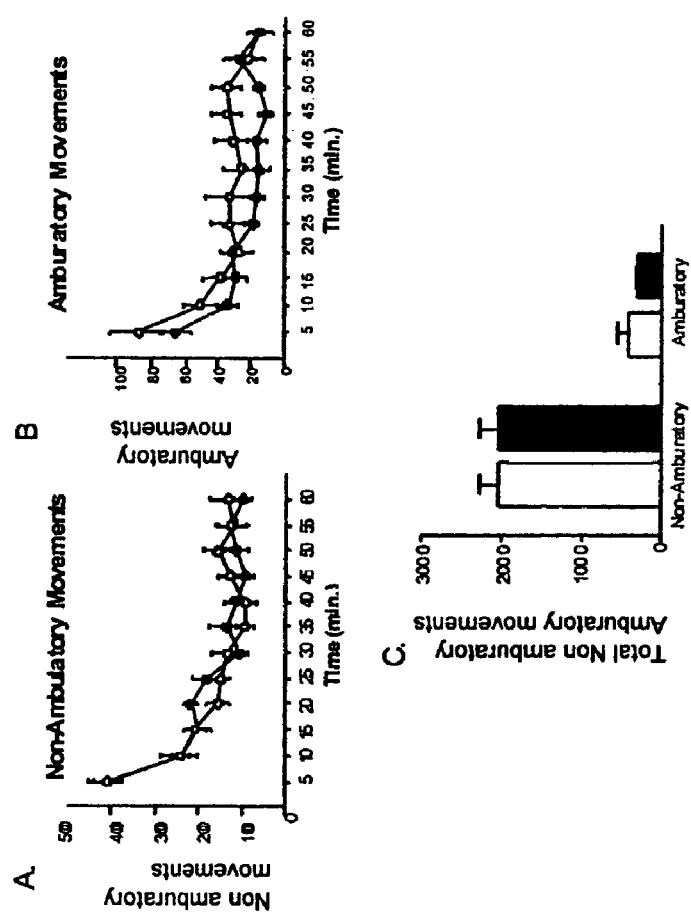
FIGS. 4A and 4B show the effect of icv administration of TPI 1361-17 on non-ambulatory (A) and ambulatory (B) movements. Both movements were monitored for one hour after the administration of 5 nmol TPI 1361-17. Open circle; ACSF injected control, n=10. Closed circle; TPI 1361-17 injected, n=10. Each data point represents the value with the S.E.M.
FIG. 4C shows sums of non-ambulatory and ambulatory movements. Open column corresponds to control; closed column corresponds to TPI 1361-17. Each column represents the mean value with S.E.M.

To determine the effect of TPI 1361-17 on spontaneous activity on rats, intraventricular cannulated rats were acclimatized to the testing situation. Five or one nmol of TPI 1361-17 administrated icv, did not exhibit any detectable changes in movement. Ambulatory movements and non-ambulatory movements were monitored for 60 minutes upon administration of five nmol TPI 1361-17 or ACSF (FIGS. 4A, 4B). Both animal groups showed highest movements just after the injection, which gradually decreased and stabilized. There were no significant differences in the total amounts of non-ambulatory or ambulatory movements under test conditions (FIG. 4C).

For these experiments, ambulatory movements were recorded using a Hamilton-Kinder Activity Monitor (with the infrared beams in a 4×8 configured frame). Locomotion was quantified in transparent polycarbonate cages (32×26×20 cm) placed within the activity frames. Animal position was detected by two dimensional beam breaks. The ambulation was tabulated as a movement that results in the change of location. All other beam breaks are categorized as non-ambulatory, fine movement. Animals were acclimatized to the novel home cage-environment for 60 minutes before injection, then were removed, injected and immediately replaced in the same cage, and monitoring began. Locomotion was measured for 60 minutes after the ICV administration of either ACSF or 5 nmol TPI 1361-17.

Figure 5:
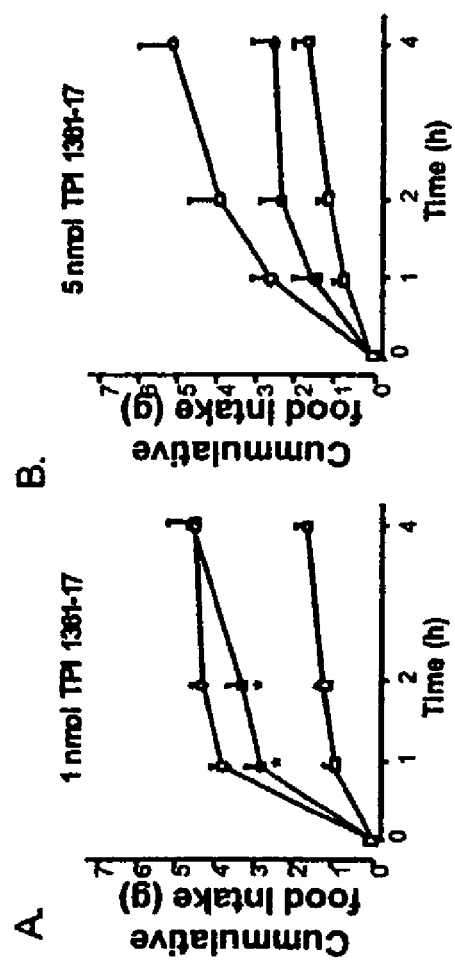
FIG. 5A shows the effect of icv administration of TPI 1361-17 on MCH-induced food intake. Rats were administered ACSF (open square, n=10), or 2 nmol MCH (open circle, n=9), or 2 nmol MCH and TPI 1361-17 (closed circle, n=9). TPI 1361-17 was tested at two doses: 1 nmol (A) and 5 nmol.
FIG. 5B shows experiments performed one to two hours into the light cycle. Ten minutes after the administration, rats were given access to regular low fat-diet, food intake was monitored and cumulative food intake was calculated. Each data point expresses mean value with S.E.M. *$p<0.05$; ANOVA/Bonferoni multiple comparison test for the effect of TPI 1361-17+MCH versus MCH alone.

To determine inhibitory effects of TPI 1361-17 on MCH-induced food intake, rats were habituated to a wire bottom cage for more than 3 weeks prior to the experiment. Experiments were carried out from 6 a.m. to 7 a.m. when rats were satiated. Intracerebroventricular injection of MCH (2 nmol) induced rapid and robust feeding in satiated rats. Addition of TPI 1361-17 (1 or 5 nmol) significantly suppressed MCH-induced food consumption in a dose dependent manner. One nmol TPI 1361-17 decreased MCH-induced food intake for 1 h and 2h but this decrease was reversed over the next two hours (FIG. 5A). On the other hand, five nmol of TPI 1361-17 suppressed cumulative food intake by 75% even at 4h (FIG. 5B).

To determine the effects of TPI 1361-17 on MCH-induced food intake, rats were randomly divided into three groups: 1) TPI 1361-17 (dissolved in DMSO) and 2 nmol of MCH; 2) MCH 2 nmol, 3) ACSF. Each mixture contained a DMSO equivalent concentration to that of the antagonist solution (up to 5% (v/v)). Ten µl of each solution was administered into lateral ventricle for 2 minutes. The injections were done between 7:00-8:00 a.m., and food intake was monitored for 4 h after the injection.

Figure 6:
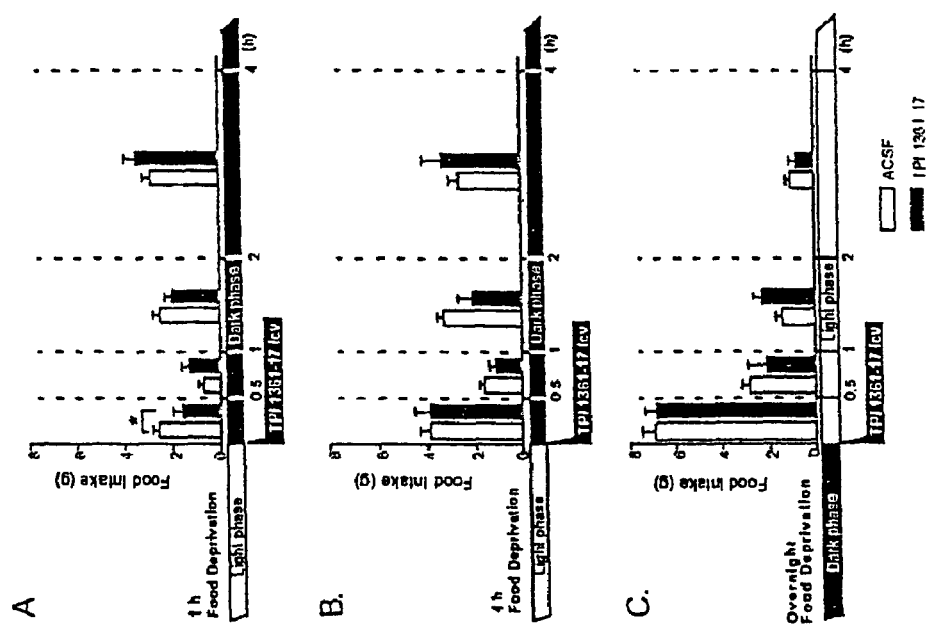
FIG. 6 shows the effect of icv administration of TPI 1361-17 on spontaneous food intake. Chow was given to rats 15 min after icv administration of 5 nmol TPI 1361-17 (n=16) or ACSF (n=17) under various conditions.
Figure 8:
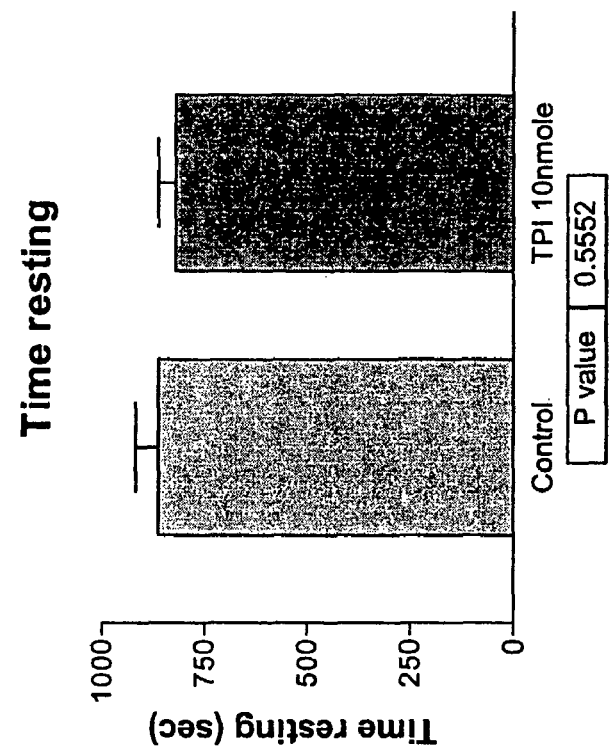
FIG. 8 is a bar graph showing the time resting of control and TPI treated rats in Example VI below.
Figure 7:
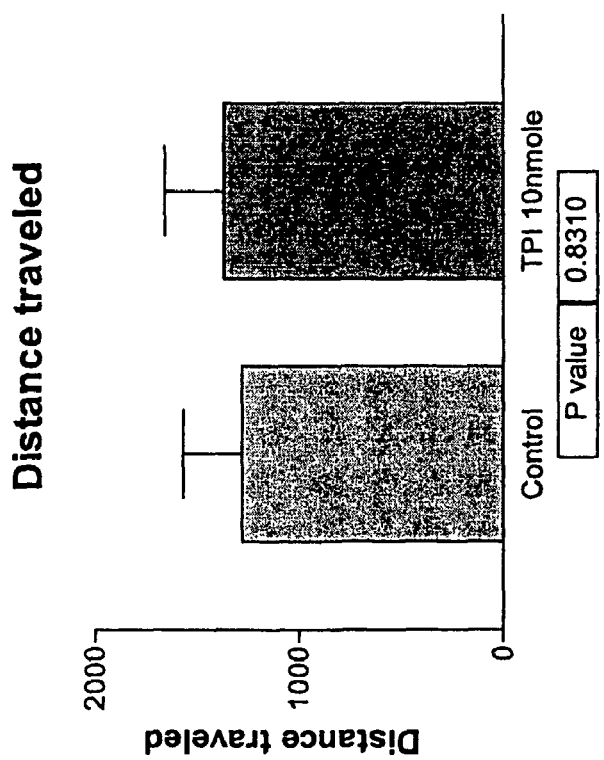
FIG. 7 is a bar graph showing distance traveled by control and TPI treated rats in Example VI below.
Figure 10:
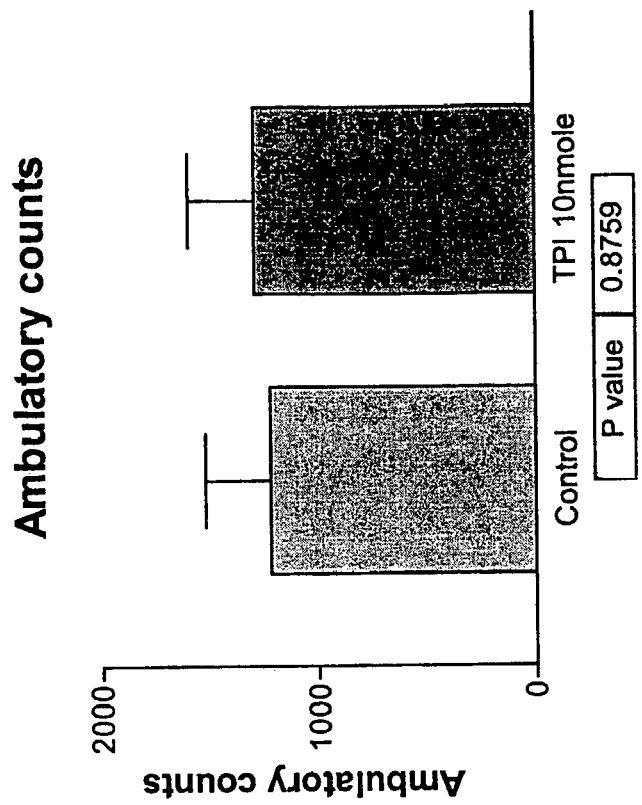
FIG. 10 is a bar graph showing ambulatory counts in control and TPI treated rats in Example VI below.
Figure 9:
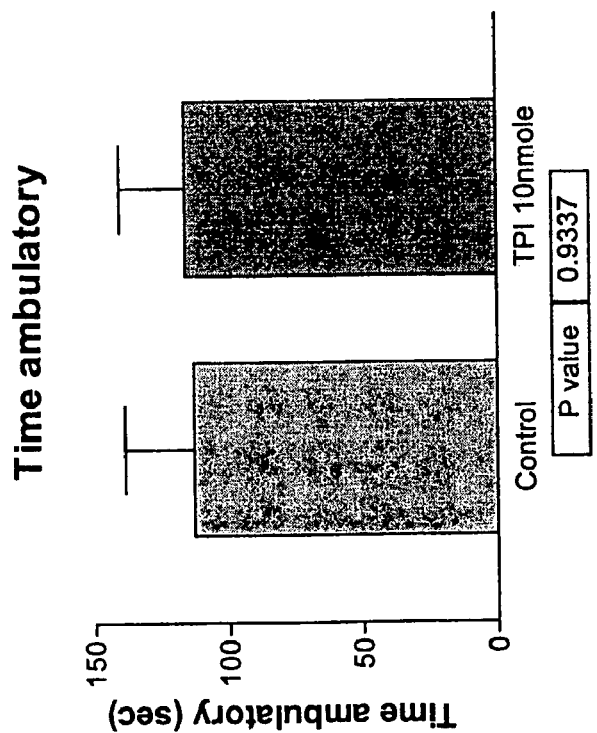
FIG. 9 is a bar graph showing the time ambulatory of control and TPI treated rats in Example VI below.
Figure 12:
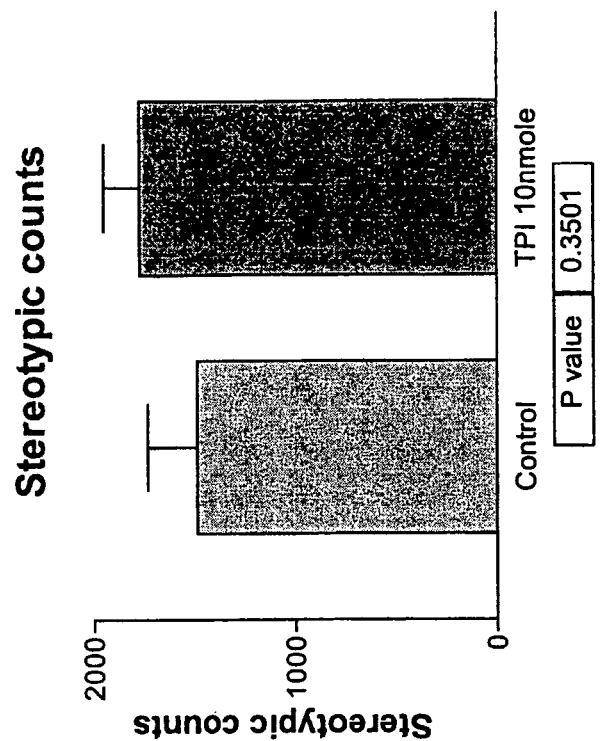
FIG. 12 is a bar graph showing stereotypic counts in control and TPI treated rats in Example VI below.
Figure 11:
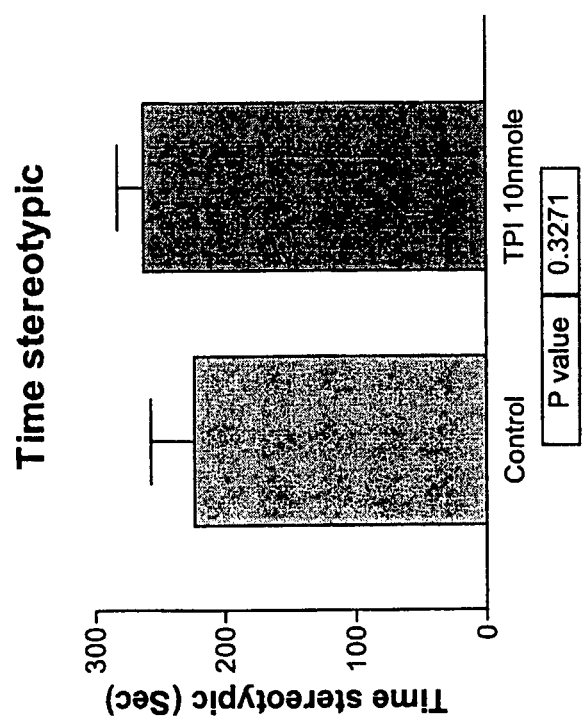
FIG. 11 is a bar graph showing time stereotypic in control and TPI treated rats in Example VI below.
Figure 14:
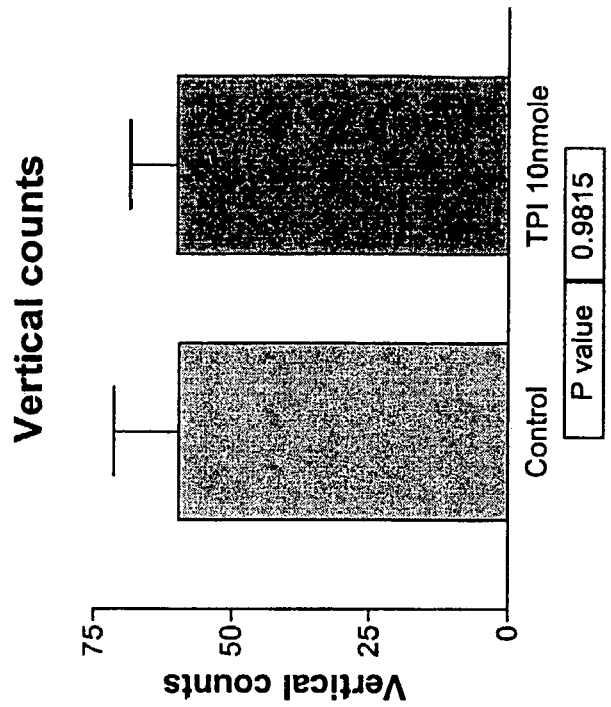
FIG. 14 is a bar graph showing vertical counts in control and TPI treated rats in Example VI below.
Figure 13:
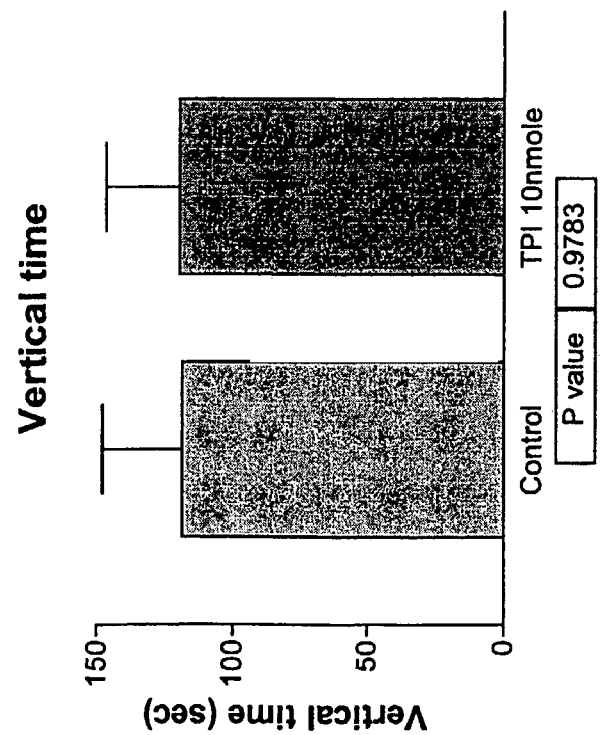
FIG. 13 is a bar graph showing vertical time in control and TPI treated rats in Example VI below.

To determine inhibitory effects of TPI 1361-17 on spontaneous food intake, TPI 1361-17 (5 nmol) was administered icv and food intake was measured 0.5 h, 1 h, 2 h, and 4 h after the injection. Food intake was quantified either at the start of either the dark phase, which is considered similar to natural conditions, or the light phase. To synchronize initiation of the food intake and to measure the efficiency of TPI 1361-17, rat food pellets were removed for different lengths of time before the injection. It was observed that TPI 1361-17 reduced spontaneous food intake of rats that have been fasted for 1 hr before the dark phase by 37%. This inhibitory effect was detected within the first 30 minutes of feeding and is not detected later (FIG. 6A). If rats were fasted for 4 h before the dark phase (FIG. 6B) or for 12 hrs before the light phase (FIG. 6C), they consumed higher quantities of chow and TPI 1361-17 had no apparent effect. These results indicate that the central blockade of the MCH1R system by TPI 1361-17 on food consumption is acute and detectable when the intake is low, i.e. when hunger is not a dominant factor.

The two groups of rats that were tested at the beginning of the dark phase were starved for 1 h or 4 h before, being injected with 5 nmol of antagonist or ACSF between 6:00-7:00 p.m. Animals had free access to water. Fifteen minutes after injection, container of regular low-fat diet were placed in the cage, and food consumption was monitored for 4 h. The group of rats that were injected at the beginning of the light phase was starved overnight before being injected at 5 nmol of antagonist or ACSF. Monitoring of the food consumption was identical to that described for the rats starved during the dark phase.

For animal studies, adult male Sprague-Dawley rats weighing 200-300g were obtained from Charles River Laboratories (Wilmington, Mass.), bearing a 23-gauge stainless steel cannula placed into the right lateral ventricle. Rats were housed individually and maintained on a 12 h light-dark cycle (6:00 am-6:00 pm light) with free access to tap water and rat chaw (PROLAB RMH 2500, containing 23.0% protein, 4.5% fat, gross energy 4.5 kcal/g. PMI nutrition international, LLC. Brentwood, Mo.). Prior to all studies, rats were handled and habituated for 7 days, and 10 µl of artificial cerebrospinal fluid (ACSF: NaCl 124, KCl 5, CaCl2 2.4 MgSO4 2, KH2PO4 1.25, NaHCO3 26 and glucose 10, in mM) was injected through the cannula to minimize stress effects at the time of the experiment. Cannula placement was confirmed in all animals by evaluating the response to 50 ng of angiotensin II. Only animals drinking more than 5 ml of water in 1 h were used in feeding studies.

EXAMPLE V

General Synthesis of N-benzylamino Imidazolidine-2-thiones and -2-ones

The N-benzylamino imidazolidine-2-thione, for example, (N-(3-{(4S)-1-[(1S)-2-(benzylamino)-1-methylethyl]-3-[2-(3-fluorophenyl)ethyl]-2-thioxoimidazolidin-4-yl}propyl) guanidine (TPI 1361-17) and -2-one compounds of the present invention can be synthesized according to the following general reaction scheme (Scheme 1):

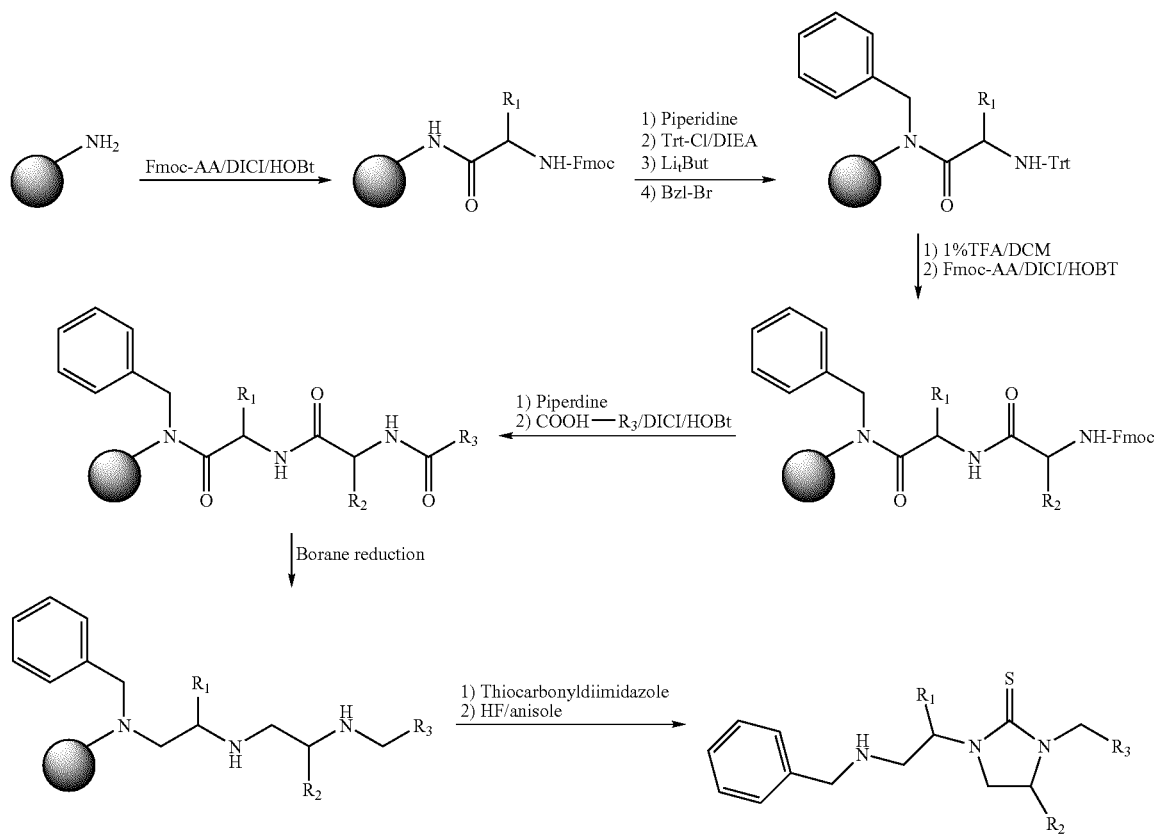

Scheme 1

The N-benzylamino imidazolidine-2-thione and -2-one compounds can be prepared according to the general scheme in Scheme 1 is described in Nefzi et al. Tetrahedron Letters, 38:931-934 (1997) as well as Nefzi, A., et al, U.S. Pat. No. 5,786,448. The N-benzylamino imidazolidine-2-thione and -2-one compounds were prepared using solid-phase techniques. The solid-phase resin, here p-methylbenzhydrylamine resin (MBHA), is indicated in Scheme 1 by the large circle and dash. With reference to Scheme 1, the first amino acid (Fmoc-AA in Scheme 1) was coupled using the conventional reagents hydroxybenzotriazole (HOBt) and diisopropylcarbodiimide (DICI). Following removal of the protecting group with 25% piperidine in DMF, the resin was shaken overnight in a solution of trityl chloride in DCM/DMF (9:1) in the presence of DIEA. N-alkylation was then performed by treatment of the resin with 1M lithium t-butoxide in THF. Excess base was removed by cannulation, followed by addition of the individual alkylating agent (Benzyl bromide in Scheme 1) in DMSO. The solution was vigorously shaken for 2 h at room temperature. The alkylating agents are those which include halogenated alkyls, substituted alkyl, cycloalkyl, substituted cycloalkyl, aralkyl or substituted aralkyl for example, a benzyl bromide, methyl iodide, ethyl iodide, allyl bromide, napthyl bromide. Other alkylating derivatives are well known. Preferably the alkylating agent is methyl iodide or benzyl bromide. This method of N-alkylation is known and has been used for the synthesis of soluble peptidomimetic combinatorial libraries through successive or exhaustive amide alkylation as described, for example, in Dorner et al. Bioorg. & Med. Chem., 4:709 (1996) and Ostresh et al. Proc, Nat. Acad. Sci., 91:11138 (1994), both of which are incorporated herein by reference.

Again with reference to Scheme 1, upon removal of the trityl group with 2% TFA in DCM (2×10 min), the packet was washed, neutralized and the second amino acid (Fmoc-M-OH in Scheme 1) was coupled. Following removal of the Fmoc group, the dipeptide was acylated with a carboxylic acid in the presence of diisopropylcarbodiimide (DICI) and 1-hydroxybenzotriazole (HOBt). An exemplary compound in which Fmoc-L-Ala was used to derive $R_1$; Fmoc-L-Arg(Pmc) was used to derive $R_2$; and 3-Fluorophenylacetic acid was used to derive $R_3$ is represented by Formula IV (TPI 1361-17). Additional exemplary amino acid and carboxylic acids are discussed in Table 2.

The next key step in the synthetic process, as shown in Scheme 1, was the reduction of the amide groups of the acylated dipeptide using boric acid (40 times) and trimethyl borate (40 times) followed by 1M $BH_3$-THF (40 times). The reaction was heated at 65° C. for 72 h, followed by quenching with MeOH. The resin was then washed with tetrahydrofuran and methanol. The amine-borane complex was disassociated by overnight treatment with piperidine at 65° C. This method has been used to generate diverse chemical libraries using the "libraries from libraries" concept as described, for instance, in Ostresh et al. Proc. Nat. Acad. Sci., 91:11138 (1994) and Cuervo et al. In Peptides, 1994, Proceedings of the 23rd European Peptide Symposium (Maia, H. L. S, ed): 465-466 (1995). The cyclizations to obtain the five-member ring (and six-member ring when $R_2$ is derived from β-Alanine and, therefore, n is two) cyclic ureas and cyclic thioureas were performed using carbonyldiimidazole and thiocarbonyldiimidazole. Alternatively, the cyclization step can be carried out using phosgene, triphosgene or thiophosgene by the procedures described, for example, in Majer and Randad, J, Org. Chem., 59:1937-1938 (1994), and Kim et al., Tetrahedron Lett., 37:5309 (1996).

Following cleavage from the resin with anhydrous HF by the procedures of Houghten et al. Int. J. Pep. Prot. Res., 27:673 (1986) in the presence of anisole, the desired products were extracted and lyophilized.

Synthesis of (N-(3-{(4S)-1-[(1S)-2-(benzylamino)-1-methylethyl]-3-[2-(3-fluorophenyl)ethyl]-2-thioxoimidazolidin-4-yl}propyl)guanidine (TPI 1361-17)

The synthesis of an exemplary compound of Formula IV (TPI 1361-17) using the general scheme outlined in Scheme 1 is described. Eighty mg of p-methylbenzhydrylamine (MBHA) resin (0.81 meq/g, 100-200 mesh) was contained within a sealed polypropylene mesh packet. Reactions were carried out in a 10 ml polyethylene bottle. Following neutralization with 5% diisopropylethylamine (DIEA) in dichloromethane (DCM), the resin was washed with DCM. The first amino acid (Fmoc-L-Ala in Scheme. 1) was coupled using the conventional reagents hydroxybenzotriazole (HOBt) and diisopropylcarbodiimide (DICI), all of which were used at a 6 fold excess over free amine in DCM that provided Fmoc-L-Ala at a 0.1M concentration for 2 hrs. Following removal of the protecting group with 25% piperidine in DMF (twice for 10 minutes each), the mesh packet was shaken overnight in a solution of trityl chloride (5 fold excess) in DCM/DMF (9:1, 0.1M) in the presence of DIEA (10 fold excess). Completeness of the trityl coupling was verified using the bromophenol blue color test as described in (Krchnak et al. Coll. Czech. Chem. Commun., 53:2542 (1988), which is incorporated herein by reference.

N-alkylation was then performed by treatment of the resin packet with 1M lithium t-butoxide (20 fold excess) in THF. Excess base was removed by cannulation, followed by addition of Benzyl Bromide (60 fold excess) in DMSO (0.5M). The solution was vigorously shaken for 2 h at room temperature. Upon removal of the trityl group with 2% TFA in DCM (twice for 10 min each), the packet was washed, neutralized and the second amino acid, Fmoc-Arg(Pmc) was coupled at 0.1M concentration using HOBt and DICI in DCM at 6 fold excess over free amine for 2 hrs. Following removal of the Fmoc group with 25% piperidine in DMF (twice for 10 minutes each), the dipeptide was acylated with the carboxylic acid, 0.1M 3-Fluorophenylacetic acid, in the presence of diisopropylcarbodiimide (DICI) and 1-hydroxybenzotriazole (HOBt) using a 6 fold excess over free amine for 2 hrs.

The reduction was performed in 50 ml Kimax® tubes under nitrogen. Boric acid (40 fold excess) and trimethyl borate (40 fold excess) were added, followed by 1M $BH_3$-THF (40 fold excess). The tubes were heated at 65° C. for 72 h, followed by quenching with MeOH. The resin was then washed with tetrahydrofuran and methanol. The amine-borane complex was disassociated by overnight treatment with piperidine at 65° C.

The cyclization occurred following treatment of the reduced acylated dipeptide overnight with thiocarbonyldiimidazole (5 fold excess, 0.5M in anhydrous dichloromethane) for thiourea formation. Following cleavage from the resin with anhydrous HF (5 mL) by the procedures of Houghten et al. Int. J. Pep. Prot. Res., 27:673 (1986) in the presence of anisole (0.1 mL), the desired product was extracted (95% Acetic acid) and lyophilized. The desired product was obtained in good yields (>70% of theoretical) and high purity (>90% by HPLC) following lyophilization. By mass spectrometry, the molecular weight of purified TPI 1361-17 was 470.26 in agreement with the calculated value.

The identity and purity of each individual intermediate and final compound was analyzed by mass spectral analysis interfaced with a liquid-chromatography system (Finnigan LCQ) and/or analytical reverse-phase high performance liquid chromatography (RP-HPLC) using a Vydac C18 column and a Beckman system Gold HPLC. The individual compounds were purified by using a Waters Milliprep 3400 preparative HPLC with a preparative Foxy fraction collector. The LCQ data obtained after purification of the exemplary compound of Formula IV is shown at page 15 of United States Patent Application Publication No. 2008/0255218 which constitutes the pre-grant publication of this patent application and which is expressly incorporated herein by reference.

EXAMPLE VI

Effects of TPI on Motor Activity in Rats

Sprague Dawley rats were randomly divided into two groups (Group I and Group II) of eight (8) rats each. The rats in Group I (n=8) received 0.9% saline by i.c.v. injection. The rats in Group II (n–8) received 10 nM TPI 1361-17 (Formula IV) by i.c.v. injection. The rats were observed for 20 minutes after the administration of saline or TPI. Once each day thereafter, for a total of _____ days, the rats were taken into a test room, allowed to acclimatize for _____ minutes, then placed in four identical chambers (43 cm×43 cm×30.5 cm) that were connected to a common interface and computer (MED Associates, Inc., St. Albans, Vt.). Horizontal movement of the rats was monitored by 16 photobeams per side evenly spaced along each wall of two adjacent sides of each test chamber. As shown in FIGS. 7-14, there were no significant differences between Group I (control) and Group II (TPI Treated) in distance traveled, time resting, time ambulatory, ambulatory counts, time stereotypic and stereotypic counts, thereby indicating that, at the dose tested, TPI did not significantly effect motor activity.

EXAMPLE VII

Effects of TPI on Conditioned Place Aversion (CPA)

Rats were randomly divided into two (2) groups of eight (8) rats each (Groups I and II). Testing was performed in four identical place-conditioning chambers (43×43×30.5 cm) connected to a common interface and computer (MED Associates, Inc., St. Albans, Vt.). Test chambers had two equal compartments, each with unique sensory cues. One compartment had black and white striped walls, a stainless-steel wire mesh floor (0.16-cm wire with 1.27-cm openings), corncob bedding, and lemon-scented water applied to the walls immediately before each test. The other compartment had white walls with black dots, stainless-steel grid floor (0.48-cm rods placed 1.6 cm apart), wood-chip bedding, and banana-scented water applied to the walls. The two compartments were separated by a middle wall with a black guillotine door in the center. All rats were weighed and acclimated to the test room for 20 min each day before being placed into the apparatus.

Figure 15:
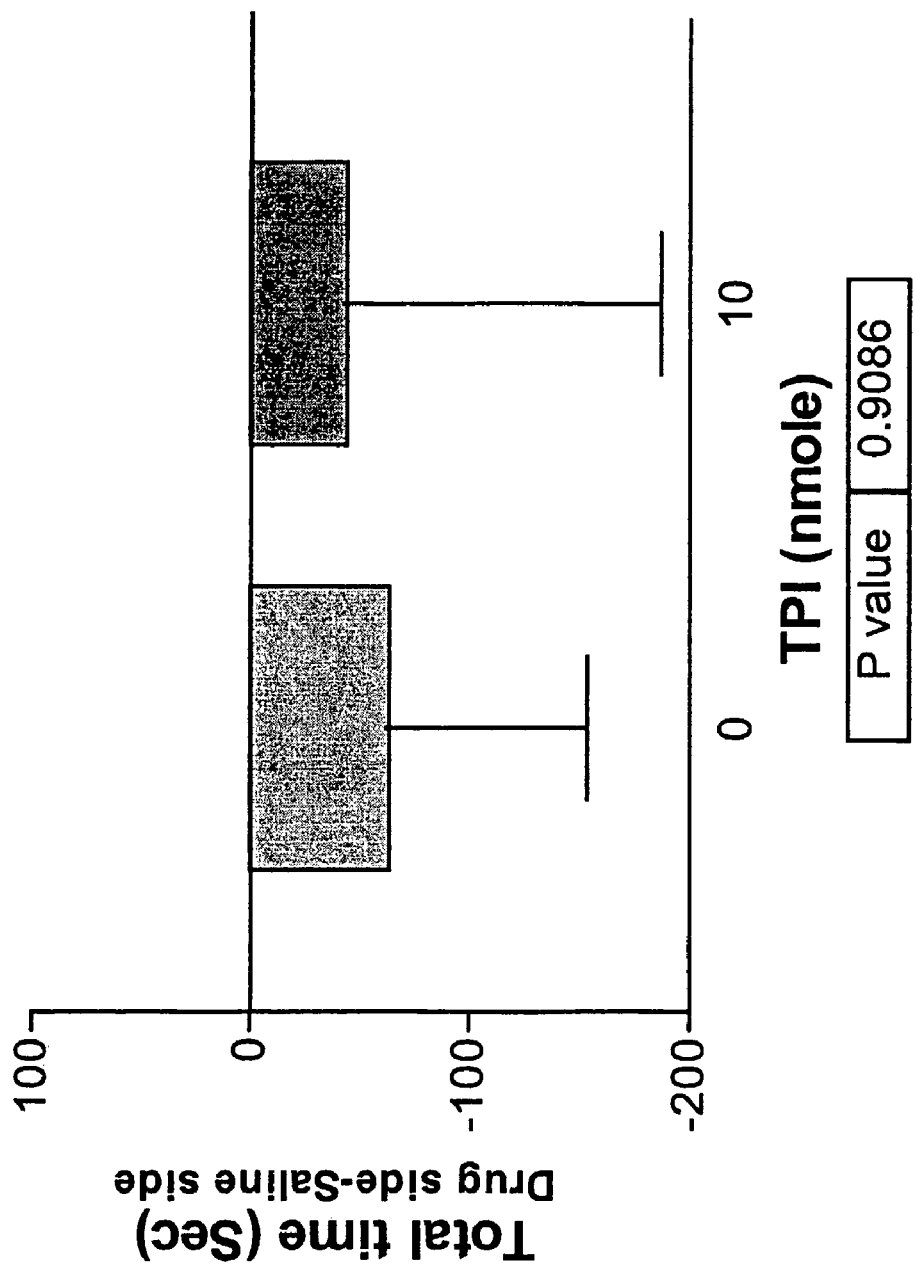
FIG. 15 is a bar graph showing a lack of conditioned place aversion (CPA) in control and TPI treated rats of Example VII below.

The CPA test consisted of three phases. During the preconditioning phase (day 1), the animals were placed into the chamber for 15 min. During the conditioning phase (day 2,3), animals were injected i.c.v with either 0 (Group I—n=8) or 10 nmole (Group 2—n=8) of TPI and confined to one side for 20 min. During the test phase (day 4), the animals received no injections and were placed in the apparatus with the guillotine door open to allow unrestricted movement in both chambers. The activity of the animals was monitored for 15 min. As shown in FIG. 15, the 10 nM doase of TPI administered in this experiment to the Group 2 animals did not cause conditioned place aversion.

EXAMPLE VIII

Effects of TPI on Spontaneous Food Intake in Rats

In this example, adult male Sprague-Dawley rats, weighing 350-400 g were randomly divided into two (2) groups of eight (8) rats each (Groups I and II). The animals were housed individually in a room having an ambient temperature of 20 degrees C., a light cycle from 07:00 to 19:00 each day and a dark cycle from 19:00 to 07:00.

Figure 17:
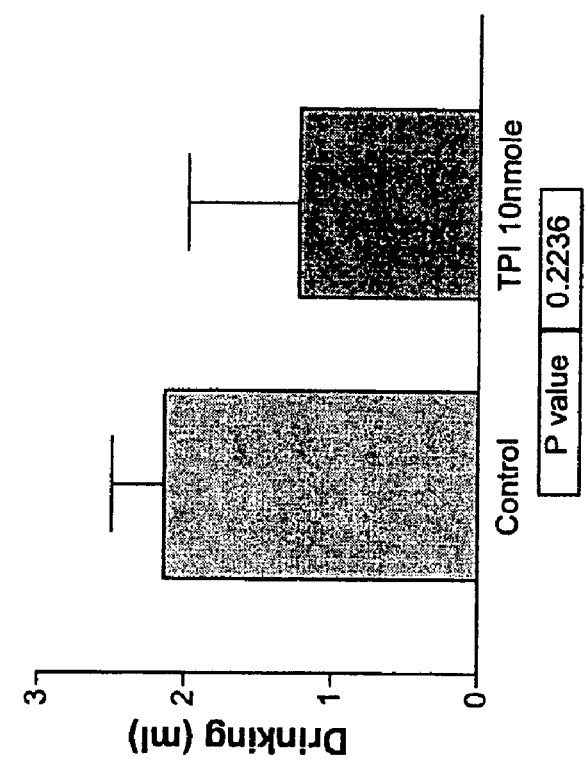
FIG. 17 is a bar graph showing a non-significant decrease in 30 minute water intake following 1 hour of food/water deprivation in TPI treated rats of Example VIII below.
Figure 16:
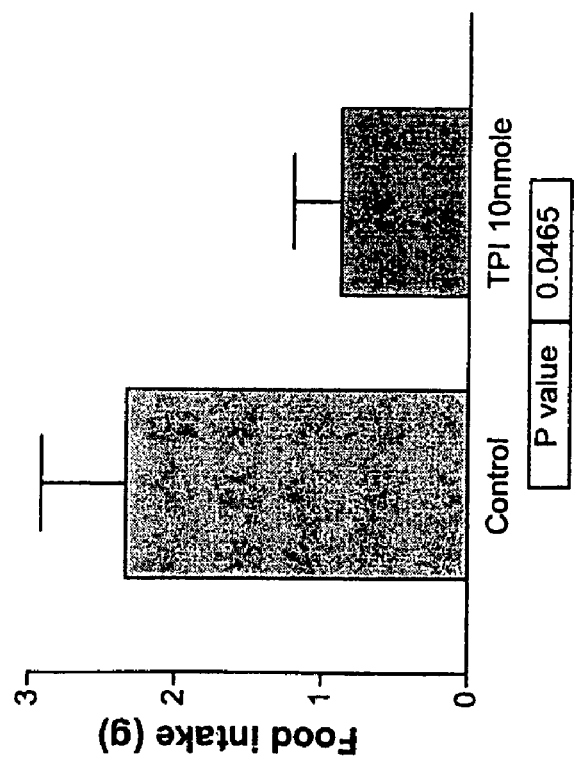
FIG. 16 is a bar graph showing a significant decrease in 30 minute food intake following 1 hour of food/water deprivation in TPI treated rats of Example VIII below.

In a first experiment, food (rat chow) and water were made available ad libitum except during a 1 hour food/water deprivation period from 18:00 to 19:00. At the end of the 1 hour food/water deprivation period the animals in Group I (n=8) received 0.9% saline by i.c.v. injection and the animals in Group II (n=8) received 10 nM TPI 1361-17 (Formula IV) by i.c.v. injection. Immediately after dosing, and upon commencement of the darkness cycle, food (rat chow) and water were again made available ad libitum and food and water intake were measured for the next thirty (30) minutes. Bar graphs representing the measured food and water intake are shown in FIGS. 16 and 17. Data were compared using the non-parametric t-Test with the 0.05 level of probability and below being defined as significant. The mean food intake in the animals of Group I (control) was significantly greater (p less than 0.005) than the mean food intake in the animals of Group II (TPI treated). The mean water intake in the animals of Group I (control) animals was also greater than the mean intake in the animals of Group II (TPI treated), but such difference was not significantly different.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is clamed is:
1. A composition of matter comprising a compound having the following structural formula:

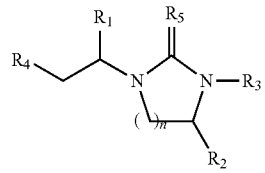

wherein,
$R_1$ and $R_2$ are selected from H, a hydrocarbyl having up to 20 carbon atoms, and a hydrocarbyl having up to 20 carbon atoms and substituted with a group selected from hydroxy, alkoxy, amino, substituted amino, thio, alkylthio, guanidino, ureido and heterocyclyl;
$R_3$ is selected from a hydrocarbyl having up to 20 carbon atoms, and a hydrocarbyl having up to 20 carbon atoms and substituted with a group selected from halo, haloalkyl, hydroxy, alkyl, alkoxy, alkylenedioxy, amino, substituted amino, aminoalkyl, thio, alkylthio, guanidino, ureido, heterocyclyl, heteroaryl, and heteroarylthio;
$R_4$ is a substituted amino, $-NR_6R_7$, wherein $R_6$ and $R_7$ are selected from H and a hydrocarbyl having up to 20 carbon atoms; $R_6$ and $R_7$, with inclusion of N, may combine to form a heterocyclic ring such as indolinyl having the formula

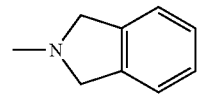

$R_5$ is selected from O, S, NH, N-alkyl, N-alkenyl, N-alkynyl, N-cycloalkyl, N-aryl and N-aralkyl,
n is 1 to 3; and
wherein the composition is further characterized by at least one additional limitation selected from group consisting of:
one or more methylene groups of a hydrocarbyl group of R3 being replaced by an oxygen atom;
$R_1$ being selected from alkyl and aminoalkyl;

$R_1$ being selected from (S)-Methyl, (R)-Methyl or (S)-Propyl;
$R_1$ being (S)-Aminopropyl;
$R_2$ being selected from (R)-Aminomethyl-(imino)-propyl, (S)-Aminomethyl-(imino)-propyl or (S)-Methylthiomethyl;
$R_3$ being selected from alkyl, aralkyl or substituted aralkyl;
$R_3$ being 3-bromophenethyl;
$R_3$ being 3,5 bis-(trifluoromethyl)phenethyl;
$R_4$ being aralkylamino;
$R_4$ being benzylamino;
$R_6$ and $R_7$ with inclusion of n, being heterocyclyl; and
—$NR_6R_7$ being isoindolinyl having the formula

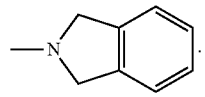

2. A composition according to claim 1, wherein R1, R2, R3, R6 or R7 comprises a straight chain hydrocarbyl.

3. A composition according to claim 1, wherein R1, R2, R3, R6 or R7 comprises a branched chain hydrocarbyl.

4. A composition according to claim 1, wherein R1, R2, R3, R6 or R7 comprises a saturated hydrocarbyl.

5. A composition according to claim 1, wherein R1, R2, R3, R6 or R7 comprises an unsaturated hydrocarbyl.

6. A composition according to claim 1, wherein R1, R2, R3, R6 or R7 comprises a cyclic hydrocarbyl.

7. A composition according to claim 1, wherein R1, R2, R3, R6 or R7 comprises an acyclic hydrocarbyl.

8. A composition according to claim 1, wherein R1, R2, R3, R6 or R7 comprises a chiral hydrocarbyl.

9. A composition according to claim 1, wherein R1, R2, R3, R6 or R7 comprises an achiral hydrocarbyl.

10. A composition according to claim 1, wherein R1, R2, R3, R6 or R7 comprises a substituted hydrocarbyl.

\* \* \* \* \*